(12) United States Patent
Peterson et al.

(10) Patent No.: US 8,491,521 B2
(45) Date of Patent: Jul. 23, 2013

(54) REMOVABLE MULTI-CHANNEL APPLICATOR NOZZLE

(75) Inventors: Michael T. Peterson, Lakeville, MN (US); Alan Van Houten, Carver, MN (US)

(73) Assignee: Celleration, Inc., Eden Prairie, MN (US)

( * ) Notice: Subject to any disclaimer, the term of this patent is extended or adjusted under 35 U.S.C. 154(b) by 120 days.

(21) Appl. No.: 12/218,760

(22) Filed: Jul. 17, 2008

(65) Prior Publication Data
US 2009/0043248 A1    Feb. 12, 2009

Related U.S. Application Data

(63) Continuation-in-part of application No. 12/006,739, filed on Jan. 4, 2008.

(60) Provisional application No. 60/878,621, filed on Jan. 4, 2007.

(51) Int. Cl.
*A61B 17/20* (2006.01)

(52) U.S. Cl.
USPC .............. 604/22; 604/275; 604/39; 604/239; 604/257; 604/258; 604/264

(58) Field of Classification Search
USPC .............. 604/264, 22, 239, 275, 257, 39, 258
See application file for complete search history.

(56) References Cited

U.S. PATENT DOCUMENTS

| | | |
|---|---|---|
| 2,534,046 A | 12/1950 | Mau |
| 2,889,852 A | 6/1959 | Dunlap |
| 3,207,181 A | 9/1965 | Elizabeth |
| 3,243,122 A | 3/1966 | Snaper |
| 3,275,059 A | 9/1966 | McCullough |

(Continued)

FOREIGN PATENT DOCUMENTS

| | | |
|---|---|---|
| CA | 2421798 | 3/2002 |
| CA | 2436812 A1 | 8/2002 |

(Continued)

OTHER PUBLICATIONS

Department of Health & Human Services Letter dated Jun. 25, 2004 (3 pages).

(Continued)

*Primary Examiner* — Kevin C Sirmons
*Assistant Examiner* — Edelmira Bosques
(74) *Attorney, Agent, or Firm* — Patterson Thuente Pedersen, P.A.

(57) ABSTRACT

An applicator for use with an ultrasound transducer assembly is disclosed. In an embodiment, an applicator includes a nozzle body having an interior and an exterior surface; a nozzle liner having an interior and an exterior surface and being engageable with the nozzle body such that a plurality of channels are defined at least in part by the exterior surface of the nozzle liner and the interior surface of the nozzle body, each of the plurality of channels having an inlet and an outlet; a passageway defined by a space between the nozzle body and the nozzle liner, in fluid communication with the inlets of each of the plurality of channels; and an opening sized and shaped for introducing fluid to the passageway to provide fluid flow from the outlet of each of the plurality of channels essentially simultaneously. Kits and methods are also disclosed.

39 Claims, 23 Drawing Sheets

U.S. PATENT DOCUMENTS

| | | | |
|---|---|---|---|
| 3,392,916 A | 7/1968 | Engstrom et al. |
| 3,433,226 A | 3/1969 | Boyd |
| 3,504,887 A | 4/1970 | Okerblom |
| 3,522,801 A | 8/1970 | Robinson |
| 3,561,444 A | 2/1971 | Boucher |
| 3,636,947 A | 1/1972 | Balamuth |
| 3,685,634 A | 8/1972 | Bergling |
| 3,685,694 A | 8/1972 | Ianelli |
| 3,765,606 A | 10/1973 | Moss et al. |
| 3,860,173 A | 1/1975 | Sata et al. |
| 3,874,372 A | 4/1975 | Le Bon |
| 3,952,918 A | 4/1976 | Poitras et al. |
| 4,052,004 A | 10/1977 | Martin et al. |
| 4,085,893 A | 4/1978 | Durley, III |
| 4,153,201 A | 5/1979 | Berger et al. |
| 4,185,502 A | 1/1980 | Frank |
| 4,192,294 A | 3/1980 | Vasilevsky et al. |
| 4,251,031 A | 2/1981 | Martin et al. |
| 4,271,705 A | 6/1981 | Crostack et al. |
| 4,294,407 A | 10/1981 | Reichl et al. |
| 4,301,093 A | 11/1981 | Eck et al. |
| 4,301,968 A | 11/1981 | Berger et al. |
| 4,309,989 A | 1/1982 | Fahim |
| 4,319,155 A | 3/1982 | Nakai et al. |
| 4,331,137 A | 5/1982 | Sarui |
| 4,334,531 A | 6/1982 | Reichl et al. |
| 4,352,459 A | 10/1982 | Berger et al. |
| 4,414,202 A | 11/1983 | Silvetti |
| 4,428,531 A | 1/1984 | Martin et al. |
| 4,466,571 A | 8/1984 | Muhlbauer et al. |
| 4,530,360 A | 7/1985 | Duarte et al. |
| 4,541,564 A | 9/1985 | Berger et al. |
| 4,551,139 A | 11/1985 | Plaas et al. |
| 4,582,149 A | 4/1986 | Slaughter, Jr. |
| 4,582,654 A | 4/1986 | Karnicky et al. |
| 4,619,400 A | 10/1986 | van der Burgt et al. |
| 4,642,581 A | 2/1987 | Erickson |
| 4,655,393 A | 4/1987 | Berger |
| 4,659,014 A | 4/1987 | Soth et al. |
| 4,679,551 A | 7/1987 | Anthony et al. |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,767,402 A | 8/1988 | Kost et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,815,661 A | 3/1989 | Anthony |
| 4,818,697 A | 4/1989 | Liboff et al. |
| 4,850,534 A * | 7/1989 | Takahashi et al. | 239/102.2 |
| 4,877,989 A | 10/1989 | Drews et al. |
| 4,883,045 A | 11/1989 | Theisz |
| 4,905,671 A | 3/1990 | Senge et al. |
| 4,930,700 A | 6/1990 | McKown |
| 4,941,614 A | 7/1990 | Ilott |
| 4,941,618 A | 7/1990 | Hildebrand et al. |
| 4,961,885 A | 10/1990 | Avrahami et al. |
| 4,982,730 A | 1/1991 | Lewis, Jr. |
| 5,002,059 A | 3/1991 | Crowley et al. |
| 5,013,241 A | 5/1991 | von Gutfeld et al. |
| 5,040,537 A | 8/1991 | Katakura et al. |
| 5,045,066 A | 9/1991 | Scheuble et al. |
| 5,062,795 A | 11/1991 | Woog |
| 5,063,922 A | 11/1991 | Hakkinen et al. |
| 5,067,655 A * | 11/1991 | Farago et al. | 239/124 |
| 5,076,266 A | 12/1991 | Babaev et al. |
| 5,104,042 A | 4/1992 | McKown |
| 5,115,805 A | 5/1992 | Bommannan et al. |
| 5,134,993 A | 8/1992 | van der Linden et al. |
| 5,143,588 A | 9/1992 | Liboff et al. |
| 5,152,289 A | 10/1992 | Viebach et al. |
| 5,163,433 A | 11/1992 | Kagawa et al. |
| 5,171,215 A | 12/1992 | Flanagan |
| 5,172,692 A | 12/1992 | Kulow et al. |
| 5,186,162 A | 2/1993 | Talish et al. |
| 5,197,946 A | 3/1993 | Tachibana et al. |
| 5,211,160 A | 5/1993 | Talish et al. |
| 5,219,401 A | 6/1993 | Cathignol et al. |
| 5,231,975 A | 8/1993 | Bommannan et al. |
| 5,259,384 A | 11/1993 | Kaufman et al. |
| 5,269,291 A | 12/1993 | Carter |
| 5,309,898 A | 5/1994 | Kaufman et al. |
| 5,314,441 A | 5/1994 | Cusack et al. |
| 5,315,998 A | 5/1994 | Tachibana et al. |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief et al. |
| 5,386,940 A * | 2/1995 | Berfield | 239/394 |
| 5,393,296 A | 2/1995 | Rattner et al. |
| 5,431,663 A | 7/1995 | Carter |
| 5,437,606 A | 8/1995 | Tsukamoto et al. |
| 5,456,258 A | 10/1995 | Kondo et al. |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,523,058 A | 6/1996 | Umemura |
| 5,527,350 A | 6/1996 | Grove et al. |
| 5,529,572 A | 6/1996 | Spector et al. |
| 5,545,124 A | 8/1996 | Krause et al. |
| 5,547,459 A | 8/1996 | Kaufman et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon et al. |
| 5,611,993 A | 3/1997 | Babaev |
| 5,616,140 A | 4/1997 | Prescott |
| 5,618,275 A | 4/1997 | Bock |
| 5,626,554 A | 5/1997 | Ryaby et al. |
| 5,630,828 A | 5/1997 | Mawhirt et al. |
| 5,643,179 A | 7/1997 | Fujimoto et al. |
| 5,656,016 A | 8/1997 | Ogden |
| 5,658,323 A | 8/1997 | Miller |
| 5,664,570 A | 9/1997 | Bishop et al. |
| 5,688,224 A | 11/1997 | Forkey et al. |
| 5,699,805 A | 12/1997 | Seward et al. |
| 5,702,360 A | 12/1997 | Dieras et al. |
| 5,707,402 A | 1/1998 | Heim |
| 5,707,403 A | 1/1998 | Grove et al. |
| 5,713,831 A | 2/1998 | Olsson |
| 5,725,494 A | 3/1998 | Brisken |
| 5,730,705 A | 3/1998 | Talish et al. |
| 5,735,811 A | 4/1998 | Brisken |
| 5,743,863 A | 4/1998 | Chapelon et al. |
| 5,752,924 A | 5/1998 | Kaufman et al. |
| 5,762,616 A | 6/1998 | Talish |
| 5,785,972 A | 7/1998 | Tyler |
| 5,807,285 A | 9/1998 | Vaitekunas et al. |
| 5,835,678 A | 11/1998 | Li et al. |
| 5,843,139 A | 12/1998 | Goedeke et al. |
| 5,863,296 A | 1/1999 | Orton |
| 5,875,976 A | 3/1999 | Nelson et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges et al. |
| 5,895,362 A | 4/1999 | Elstrom et al. |
| 5,904,659 A | 5/1999 | Duarte et al. |
| 5,947,921 A | 9/1999 | Johnson et al. |
| 5,957,882 A * | 9/1999 | Nita et al. | 604/22 |
| 5,960,792 A | 10/1999 | Lloyd et al. |
| 5,964,223 A * | 10/1999 | Baran | 128/207.14 |
| 5,989,245 A | 11/1999 | Prescott |
| 6,001,069 A | 12/1999 | Tachibana et al. |
| 6,007,499 A | 12/1999 | Martin et al. |
| 6,014,970 A | 1/2000 | Ivri et al. |
| 6,024,718 A | 2/2000 | Chen et al. |
| 6,026,808 A | 2/2000 | Armer et al. |
| 6,027,495 A | 2/2000 | Miller |

| | | |
|---|---|---|
| 6,036,661 A | 3/2000 | Schwarze et al. |
| 6,041,253 A | 3/2000 | Kost et al. |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,104,952 A | 8/2000 | Tu et al. |
| 6,106,547 A | 8/2000 | Huei-Jung et al. |
| 6,113,558 A | 9/2000 | Rosenschein et al. |
| 6,113,570 A | 9/2000 | Siegel et al. |
| RE36,939 E | 10/2000 | Tachibana et al. |
| 6,139,320 A | 10/2000 | Hahn |
| 6,158,388 A | 12/2000 | Wenstrand |
| 6,158,431 A | 12/2000 | Poole |
| 6,161,536 A | 12/2000 | Redmon et al. |
| 6,176,839 B1 | 1/2001 | Deluis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,254,294 B1 | 7/2001 | Muhar |
| 6,273,864 B1 | 8/2001 | Duarte et al. |
| 6,296,630 B1 | 10/2001 | Altman et al. |
| 6,311,573 B1 | 11/2001 | Bhardwaj |
| 6,314,318 B1 | 11/2001 | Petty |
| 6,321,109 B2 | 11/2001 | Ben-Haim et al. |
| 6,322,527 B1 | 11/2001 | Talish |
| 6,325,769 B1 | 12/2001 | Klopotek |
| 6,392,327 B1 | 5/2002 | Lewis et al. |
| 6,450,417 B1 | 9/2002 | Gipson et al. |
| 6,458,109 B1 | 10/2002 | Henley et al. |
| 6,478,754 B1 | 11/2002 | Babaev |
| 6,500,133 B2 | 12/2002 | Martin et al. |
| 6,533,484 B1 | 3/2003 | Osei et al. |
| 6,533,803 B2 | 3/2003 | Babaev |
| 6,559,365 B2 | 5/2003 | Wilfer |
| 6,565,521 B1 | 5/2003 | Silberg |
| 6,569,099 B1 | 5/2003 | Babaev |
| 6,583,071 B1 | 6/2003 | Weidman et al. |
| 6,601,581 B1 | 8/2003 | Babaev |
| 6,623,444 B2 | 9/2003 | Babaev |
| 6,659,365 B2 | 12/2003 | Gipson et al. |
| 6,663,554 B2 | 12/2003 | Babaev |
| 6,666,431 B2 | 12/2003 | McCusker |
| 6,723,064 B2 | 4/2004 | Babaev |
| 6,732,744 B2 | 5/2004 | Olshavsky et al. |
| 6,761,729 B2 | 7/2004 | Babaev |
| 6,772,967 B1 | 8/2004 | Bontems |
| 6,830,556 B2 * | 12/2004 | Harmon et al. ............. 604/35 |
| 6,905,473 B2 | 6/2005 | Savrasov et al. |
| 6,916,296 B2 | 7/2005 | Soring et al. |
| 6,960,173 B2 | 11/2005 | Babaev |
| 6,964,647 B1 | 11/2005 | Babaev |
| 6,979,670 B1 | 12/2005 | Lyngstadaas et al. |
| 7,025,735 B2 | 4/2006 | Soring et al. |
| 7,316,664 B2 | 1/2008 | Kadziauskas et al. |
| 7,431,704 B2 | 10/2008 | Babaev |
| 7,572,268 B2 | 8/2009 | Babaev |
| 7,662,177 B2 | 2/2010 | Babaev |
| 7,713,218 B2 | 5/2010 | Babaev et al. |
| 7,729,779 B2 | 6/2010 | Babaev |
| 7,753,285 B2 | 7/2010 | Babaev |
| 7,780,095 B2 | 8/2010 | Babaev |
| 7,785,277 B2 | 8/2010 | Babaev et al. |
| 7,785,278 B2 | 8/2010 | Babaev |
| 7,830,070 B2 | 11/2010 | Babaev |
| 7,914,470 B2 | 3/2011 | Babaev |
| 2002/0016557 A1 | 2/2002 | Duarte et al. |
| 2002/0062093 A1 | 5/2002 | Soring et al. |
| 2002/0080206 A1 | 6/2002 | Lin |
| 2002/0103448 A1 | 8/2002 | Babaev |
| 2002/0138036 A1 | 9/2002 | Babaev |
| 2002/0150539 A1 | 10/2002 | Unger |
| 2002/0156400 A1 * | 10/2002 | Babaev ............................. 601/2 |
| 2002/0156414 A1 | 10/2002 | Redding et al. |
| 2002/0177846 A1 | 11/2002 | Mulier et al. |
| 2002/0182246 A1 | 12/2002 | Oyaski |
| 2003/0023193 A1 | 1/2003 | Soring |
| 2003/0125660 A1 | 7/2003 | Moutafis et al. |
| 2003/0144627 A1 | 7/2003 | Woehr et al. |
| 2003/0153961 A1 | 8/2003 | Babaev |
| 2003/0171701 A1 | 9/2003 | Babaev |
| 2003/0195644 A1 | 10/2003 | Borders et al. |
| 2003/0216687 A1 | 11/2003 | Hwang |
| 2003/0236539 A1 | 12/2003 | Rabiner et al. |
| 2003/0236560 A1 | 12/2003 | Babaev |
| 2004/0015105 A1 | 1/2004 | Ito et al. |
| 2004/0028552 A1 | 2/2004 | Bhardwaj et al. |
| 2004/0030254 A1 | 2/2004 | Babaev |
| 2004/0034982 A1 | 2/2004 | Wieber et al. |
| 2004/0055376 A1 | 3/2004 | Thompson et al. |
| 2004/0068297 A1 | 4/2004 | Palti |
| 2004/0073175 A1 | 4/2004 | Jacobson et al. |
| 2004/0076175 A1 | 4/2004 | Patenaude |
| 2004/0091541 A1 | 5/2004 | Unger |
| 2004/0186384 A1 * | 9/2004 | Babaev ............................. 600/489 |
| 2005/0075587 A1 | 4/2005 | Vago |
| 2005/0075620 A1 | 4/2005 | Iger |
| 2006/0025716 A1 | 2/2006 | Babaev |
| 2006/0058710 A1 | 3/2006 | Babaev |
| 2006/0100550 A1 | 5/2006 | Schultheiss et al. |
| 2007/0016110 A1 | 1/2007 | Babaev et al. |
| 2007/0088245 A1 | 4/2007 | Babaev et al. |
| 2007/0090205 A1 * | 4/2007 | Kunze et al. ............. 239/338 |
| 2007/0299369 A1 | 12/2007 | Babaev |
| 2008/0051693 A1 | 2/2008 | Babaev |
| 2008/0132888 A1 * | 6/2008 | Iida et al. .................. 606/41 |
| 2008/0161884 A1 | 7/2008 | Chandler et al. |
| 2008/0177221 A1 | 7/2008 | Millerd et al. |
| 2008/0183109 A1 | 7/2008 | Babaev |
| 2008/0183200 A1 | 7/2008 | Babaev |
| 2008/0214965 A1 * | 9/2008 | Peterson et al. ............. 601/2 |
| 2008/0243047 A1 | 10/2008 | Babaev |
| 2008/0243048 A1 | 10/2008 | Babaev |
| 2008/0294073 A1 | 11/2008 | Barthe et al. |
| 2008/0306501 A1 | 12/2008 | Babaev |
| 2009/0018491 A1 | 1/2009 | Babaev |
| 2009/0018492 A1 | 1/2009 | Babaev |
| 2009/0024076 A1 | 1/2009 | Babaev |
| 2009/0177122 A1 | 7/2009 | Peterson |
| 2009/0177123 A1 | 7/2009 | Peterson |
| 2009/0187136 A1 | 7/2009 | Babaev |
| 2009/0200394 A1 | 8/2009 | Babaev |
| 2009/0200396 A1 | 8/2009 | Babaev |
| 2009/0222037 A1 | 9/2009 | Babaev |
| 2009/0254005 A1 | 10/2009 | Babaev |
| 2010/0022919 A1 | 1/2010 | Peterson |
| 2010/0076349 A1 | 3/2010 | Babaev |
| 2011/0230795 A1 | 9/2011 | Babaev |

FOREIGN PATENT DOCUMENTS

| | | |
|---|---|---|
| CN | 1466445 T | 1/2004 |
| EP | 0 202 844 | 11/1986 |
| EP | 0 416 106 | 3/1991 |
| EP | 0 437 155 B1 | 2/1995 |
| EP | 0 657 226 B1 | 4/1998 |
| EP | 0 619 104 | 3/2002 |
| EP | 1 564 009 A2 | 8/2005 |
| GB | 2 099 710 A | 12/1982 |
| GB | 2 101 500 A | 1/1983 |
| JP | 3-73168 | 8/1989 |
| JP | 417844 | 5/1990 |
| JP | 09135908 A | 5/1997 |
| JP | 2000237275 | 9/2000 |
| RU | 1827239 | 7/1993 |
| SU | 878268 | 11/1981 |
| SU | 0910157 | 3/1982 |
| SU | 11064585 | 10/1982 |
| SU | 1176968 A1 | 9/1985 |
| SU | 1237261 A2 | 6/1986 |
| SU | 1704847 A2 | 1/1992 |
| WO | WO 94/06380 | 3/1994 |

| WO | WO-96/35383 | 11/1996 |
| WO | WO-97/17933 | 5/1997 |
| WO | WO 02/24150 | 3/2002 |
| WO | WO-02/24150 | 3/2002 |
| WO | WO-02/28350 | 4/2002 |
| WO | WO 02/060525 | 8/2002 |
| WO | WO02/095675 | 11/2002 |
| WO | WO 2007/002598 | 1/2007 |

OTHER PUBLICATIONS

Department of Health and Human Services Letter dated May 17, 2005 (2 pages).
International Search Report dated Oct. 1, 2004. 5 pages.
Application and File history for U.S. Appl. No. 09/669,312, filed Jan. 12, 2001. Inventors: Eilaz Babaev, pp. 1-208.
Application and File History for U.S. Appl. No. 09/774,145, filed Jan. 30, 2001. Inventors: Eilaz Babaev, pp. 1-262.
Application and File History for U.S. Appl. No. 09/684,044, filed Oct. 6, 2002. Inventors: Eilaz Babaev, pp. 1-502.
Application and File History for U.S. Appl. No. 10/409,272, filed Apr. 7, 2003. Inventors: Eilaz Babaev, pp. 1-121.
Application and File History for U.S. Appl. No. 10/815,384, filed Apr. 1, 2004. Inventors: Eilaz Babaev, pp. 1-181.
Application and File History for U.S. Appl. No. 11/168,620, filed Jun. 27, 2005. Inventors: Eilaz Babaev, Michael T. Peterson, Alan Van Houten, Greg Doten, pp. 1-176.
Application and File History for U.S. Appl. No. 11/207,334, filed Aug. 18, 2005. Inventor: Eilaz Babaev, pp. 1-71.
Application and File History for U.S. Appl. No. 11/232,801, filed Sep. 22, 2005. Inventor: Eilaz Babaev, pp. 1-269.
Application and File History for U.S. Appl. No. 11/473,934, filed Jun. 23, 2006. Inventors: Eilaz Babaev, Alan Van Houten, Michael T. Peterson, Greg Doten, pp. 1-194.
Application and File History for U.S. Appl. No. 12/004,636, filed Dec. 21, 2007. Inventors: Donald L. Millerd, Alan Van Houten, Michael T. Peterson, Ryan Tetzloff, pp. 1-118.
Application and File History for U.S. Appl. No. 12/006,739, filed Jan. 4, 2008. Inventors: Michael T. Peterson, Alan Van Houten, pp. 1-174.
U.S. Appl. No. 90/007,613, filed Jul. 5, 2005, Babaev.
Ennis, W.J., et al., "Ultrasound Therapy for Recalcitrant Diabetic Foot Ulcers: Results of a Randomized, Double-Blind, Controlled, Multicenter Study," Ostomy/Wound Management, 51(8):24-39 (2005).
European Search Report corresponding to EPO Appln. No. 01973544.8-2107-US0130096, Sep. 13, 2004.
Iraniha, S., et al., "Determination of Burn Depth With Noncontact Ultrasonography," J. Burn Care Rehabil., 21:333-338 (2000).
Zharov, V.P., et al., "Design and Application of Low-frequency Ultrasound and Its Combination with Laser Radiation in Surgery and Therapy," Critical Reviews in Biomedical Engineering, 502-519 (2001).
Zharov, V.P., et al., "Comparison possibilities of ultrasound and its combination with laser in surgery and therapy," Biomedical Optoacoustics, Proceedings of SPIE, 3916:331-339 (2000).
International Search Report for PCT/US04/010448, Application Advanced Medical Applications Inc., dated Oct. 1, 2004.
Asakawa, M., et al., "WBN/Kob-Ht Rats Spontaneously Develop Dermatitis Under Conventional Conditions: Another Possible Model for Atopic Dermatitis," Ex. Anim., 54(5): 461-465 (2005).
Bisno, A.L., et al., "Murine Model of Recurrent Group G Streptococcal Cellulitis: No Evidence of Proective Immunity," Infection and Immunity, 65(12): 4926-4930 (1997).
Brooks, R.R., et al., "Canine Carrageenin-Induced Actue Paw Inflammation Model and its Response to Nonsteroidal Antiinflammatory Drugs," J. Parmacol Methods, 25: 275-283 (1991).
Chen, L., et al., The Disease Progression in the Keratin 14 IL-4-transgenic Mouse Model of Atopic Dermatitis Parallels the Up-regulation of B Cell Activation Molecules, Proliferation and Surface and Serum IgE, Clin, Exp. Immunolo, 142: 21-30 (2005).
Dong, C., et al., "MAP Kinases in the Immune Response," Annu. Rev. Immunol., 20: 55-72 (2002).

Hammer, R.E., et al., "Spontaneous Inflammatory Disease in Transgenic Rats Expressing HLA-B27 and Himan $\beta_2$m: An Animal Model of HLA-B27-Associated Human Disorders," Cell, 63: 1099-1112 (1990).
Haqqi, T.M., et al., "Restricted Heterogeneity in T-cell Antigen Receptor V$\beta$ Gene Usage in the Lymph Nodes and Arthritic Joints of Mice," PNAS, 89: 1253-1255 (1992).
Hurvitz, A.I., "Animal Model of Human Disease, Pemphigus Vulgaris, Animal Model: Canine Pemphigus Vulgaris," American Journal of Pathology, 98(3): 861-864 (1980).
Joe, B., et al., "Animal Models of Rheumatoid Arthritis," Molecular Medicine Today, 5: 367-369 (1999).
Keffer, J., et al., "Transgenic Mice Expressing Human Tumour Necrosis Factor: A Predictive Genetic Model of Arthritis," EMBO Journal, 10(13): 4025-4031 (1991).
Liu, Z., et al., "Immunopathological Mechanism of Acantholysis in Pemphigus Vulgaris: An Explanation by Ultrastructural Observations," Society for Investigative Dermatology, DOI: 10.1111/j.0022-202X.2004.22438.x (2004).
Nishimuta, K., et al., "Effects of Metronidazole and Tinidazole Ointments on Models for Inflammatory Dermatitis in Mice," Arch. Dermatol. Res., 294: 544-551 (2003).
Pelletier, J.P., et al., "In vivo Suppression of Early Experimental Osteoarthritis by Interleukin-1 Receptor Antagonist Using Gene Therapy," Arthritis Rheum., 40(6): 1012-1019 (1997).
Schon, M.P., "Animal Models of Psoriasis—What Can We Learn from Them?," J. Invest. Dermatol., 112(4): 405-410 (1999).
Trentham, D.E., et al., Autoimmunity to Type II Collagen: An Experimental Medicine, 146: 857-868 (1977).
Wooley, P.H., et al., "Type II Collagen-Induced Arthritis in Mice, I. Major Histocompatibility Complex (I Region) Linkage and Antibody Correlatesm," J. Exp. Med., 154: 688-700 (1981).
Yamamoto, T., "Characteristics of Animal Models for Scieroderma," Current Rheumatoloty Review, 1: 101-109 (2005).
Clark (1996), The Molecular and Cellular Biology of Wound Repair, New York, NY, Plenum, pp. 3-50.
Janeway and Medzhitov (2002), Annual Review of Immunology 20: 197-216.
Application and File History of U.S. Appl. No. 90/007,613, now Ex Parte Reexamination Certificate No. 6,569,099 C1, Inventor Babaev, filed Jul. 5, 2005.
Application and File History of U.S. Appl. No. 09/669,312, Inventor Babaev, filed Sep. 25, 2000.
Application and File History of U.S. Appl. No. 09/684,044, Inventor Babaev, filed Oct. 6, 2000.
Application and File History of U.S. Appl. No. 09/774,145, Inventor Babaev, filed Jan. 30, 2001.
Application and File History of U.S. Appl. No. 10/815,384, Inventor Babaev, filed Apr. 1, 2004.
Application and File History of U.S. Appl. No. 11/168,620, Inventor Babaev et al., filed Jun. 27, 2005.
Application and File History of U.S. Appl. No. 11/207,334, Inventor Babaev, filed Aug. 18, 2005.
Application and File History of U.S. Appl. No. 11/232,801, Inventor Babaev, filed Sep. 22, 2005.
Application and File History of U.S. Appl. No. 11/473,934, Inventor Babaev et al., filed Jun. 23, 2006.
Application and File History of U.S. Appl. No. 12/004,636, Inventor Millerd et al. filed Dec. 21, 2007.
Application and File History of U.S. Appl. No. 12/006,739, Inventor Peterson et al., filed Jan. 4, 2008.
Application and File History of U.S. Appl. No. 12/507,289, filed Jul. 22, 2009, inventor Peterson.
Application and File History of U.S. Appl. No. 10/409,272, Inventor Babaev, filed Apr. 7, 2003.
Application and File History of U.S. Appl. No. 13/073,863, Inventor Babaev et al., filed Mar. 28, 2011.
Application and File History of U.S. Application No. 12/317,588, filed Dec. 23, 2008, inventor Peterson.
Application and File History for U.S. Appl. No. 12/317,710, Inventor Peterson, filed Dec. 23, 2008.
International Search Report for PCT/US02/02724, Application Advanced Medical Applications Inc., dated Dec. 11, 2002.

Office Action, dated Nov. 2, 2009, for Canadian App. 2,521,117.
Office Action, dated Sep. 26, 2007, for Canadian App. 2,521,117.
Office Action, dated Aug. 5, 2009, for Canadian App. 2,421,798.
Office Action, dated Aug. 14, 2007, for Canadian App. 2,421,798.
Office Action, dated May 18, 2006, for Canadian App. 2,421,798.
Office Action, dated Jan. 18, 2008, for Chinese App. 01816263.0.
Office Action, dated Apr. 20, 2007, for Chinese App. 01816263.0.
Summary of Office Action, dated Jul. 7, 2008, for Mexican App. PA/a/2003/002535. Machine translation provided.
Summary of Office Action, dated Apr. 25, 2006, for Mexican App. PA/a/2003/002535. Machine Translation provided.
International Search Report for PCT/US01/30096, dated Sep. 25, 2002.
European Supplementary Search Report corresponding to EP App. No. 01973544, dated Sep. 1, 2004.
International Search Report for PCT/US2004/010448, dated Nov. 10, 2004.
Examination Report, dated Dec. 5, 2007, for Indian App. 1078/MUMNP/2005.
International Search Report for PCT/US01/31226, dated Sep. 11, 2002.
International Search Report for PCT/US02/02724, dated Dec. 11, 2002.
Examination Report, dated Jul. 1, 2008, for App. 02709235.2-2305.
Examination Report, dated Nov. 21, 2007, for App. 02709235.2-2305.
European Search Report for App. 02709235.2-2305., dated Apr. 18, 2006.
Office Action, dated Jan. 14, 2010, for Canadian App. 2,436,812.
Office Action, dated May 3, 2006, for Canadian App. 2,436,812.
European Search Report for App. 02709235, dated Apr. 4, 2006.
International Search Report for PCT/US06/24833, dated Feb. 22, 2007.
Written Opinion for International Application No. PCT/US06/24833, dated Feb. 22, 2007.
Japanese Office Action, dated Jul. 29, 2010 for Japanese Application No. 2002-528187.
International Search Report for PCT/US95/14926, dated Feb. 27, 1996.
Japanese Office Action, dated Dec. 18, 2009 for Japanese Application No. 2002-528187.
International Search Report for PCT/US2008/000151, dated Apr. 21, 2008.
Chinese Office Action, dated May 22, 2009 for Chinese Application No. 2006-800227860.
International Search Report for PCT/US2007/026251, dated May 7, 2008.
International Search Report for EP 04749758.1-2319, dated Mar. 30, 2011.
International Search Report for EP 04749758.1-2319, dated Apr. 30, 2010.
Office Action, dated Sep. 12, 2006, for Canadian App. 2,463,600.
European Examination Report for Application No. 01 973 554.8, dated Feb. 9, 2010.
European Examination Report for Application No. 08 866 666.4, dated Mar. 22, 2011.
Office Action mailed Apr. 24, 2007, for Japanese App. No. 2002-560715 now JP-4,164,582.
European Supplementary Search Report corresponding to EP App. No. 02709235, dated Apr. 4, 2006.
Japanese Notification of Reasons for Rejection from Japanese Application No. 2008-518499 dated Jul. 29, 2011.
European Office Action dated Dec. 16, 2011 for EP 01973544.8.
Weichental et al., "Low-Frequency Ultrasound Treatment of Chronic Venous Ulcers", Wound Repair and Regeneration. vol. 5, No. 1. Jan.-Mar. 1997.
Dyson et al., "Stimulation of Healing of Varicose Ulcers by Ultrasound", Ultrasonics. Sep. 1976.
Voight et al., "Low-Frequency Ultrasound (20-40 kHz) as an Adjunctive Therapy for Chronic Wound Healing: A Systematic Review of the Literature and Meta-Analysis of Eight Randomized Controlled Trials", The International Journal of Lower Extremity Wounds. 10(4) 190-199. Dec. 2011.

* cited by examiner

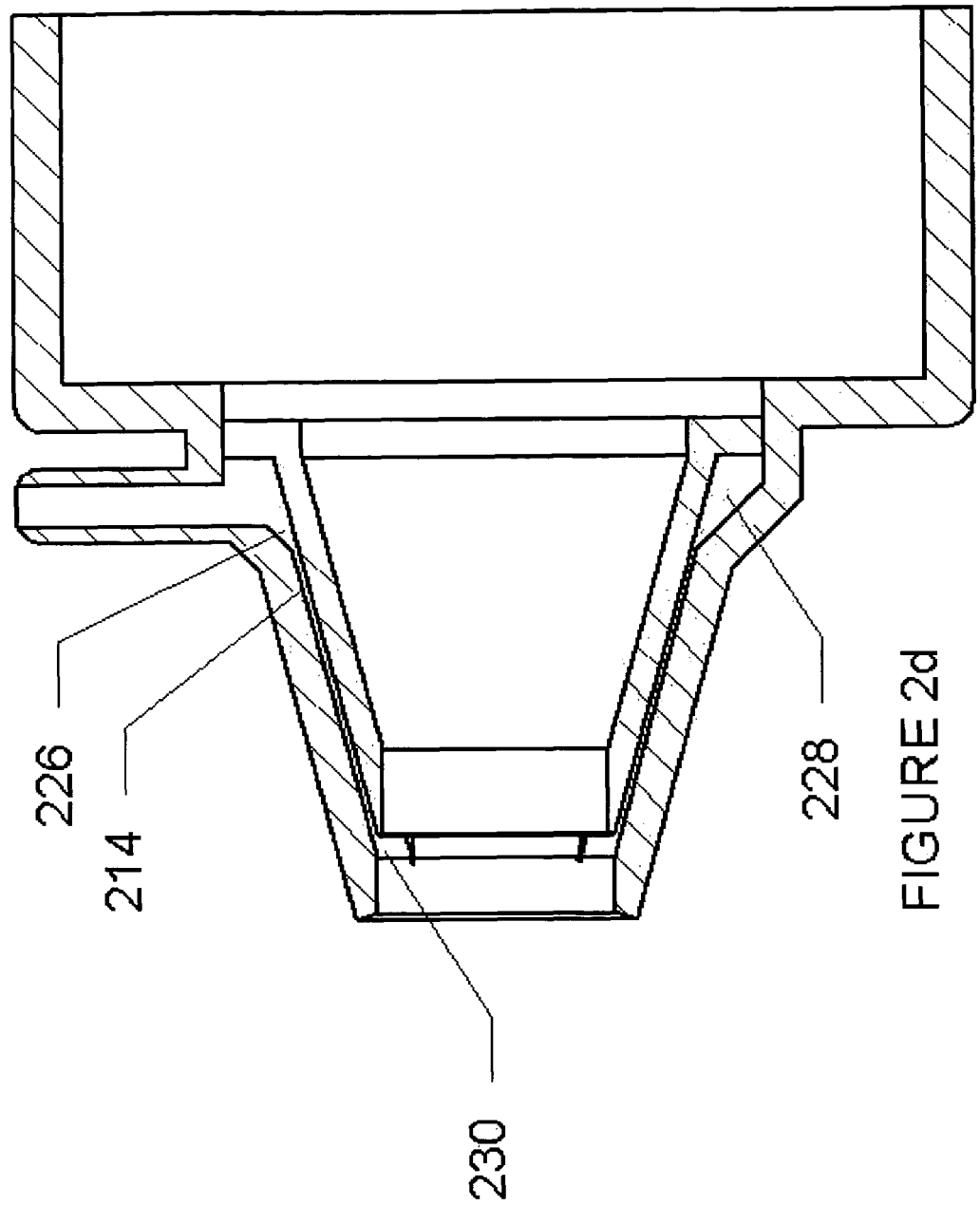

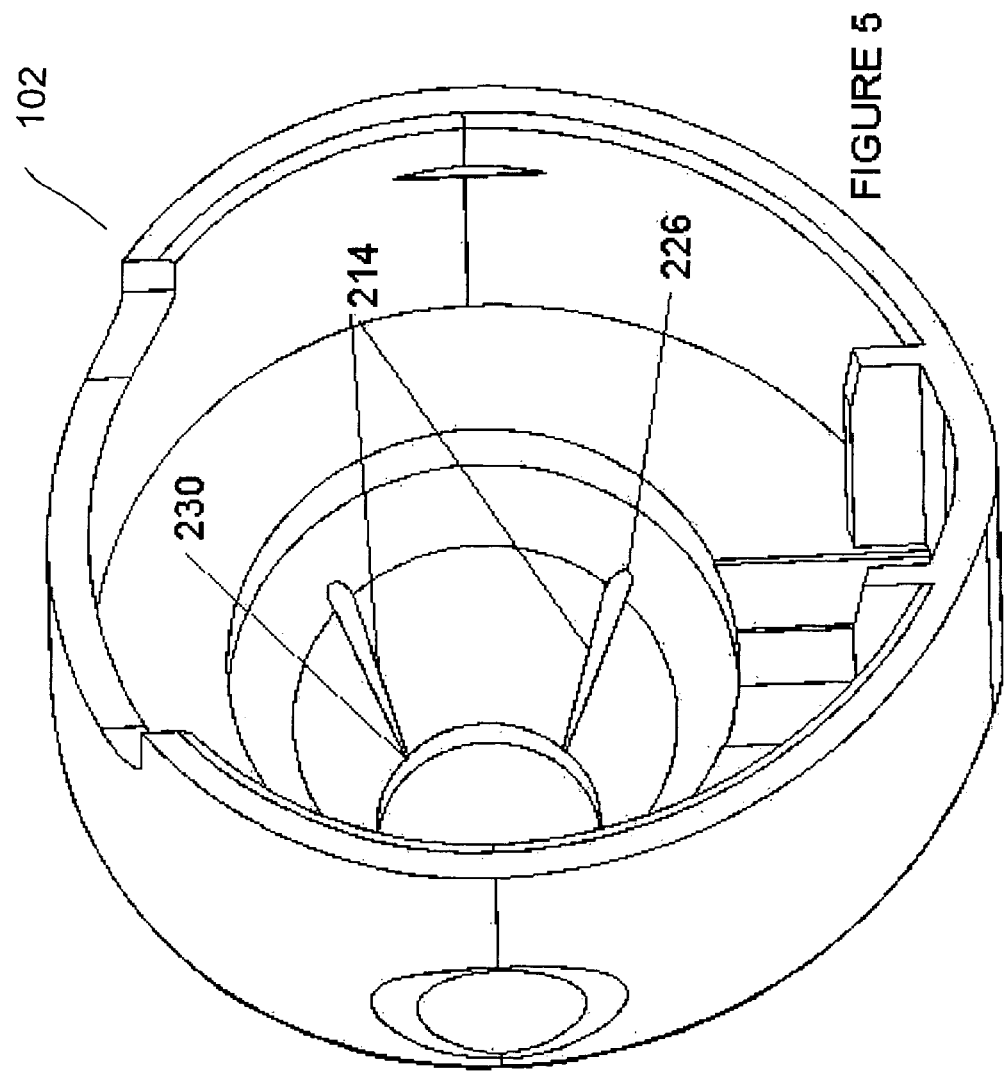

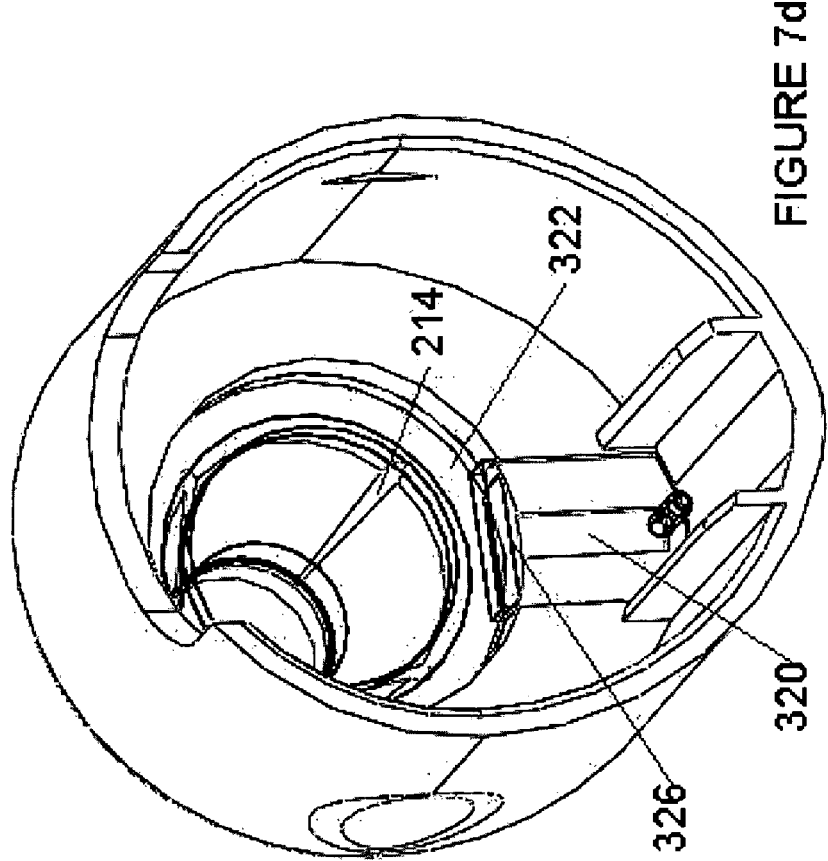

US 8,491,521 B2

REMOVABLE MULTI-CHANNEL APPLICATOR NOZZLE

RELATED APPLICATIONS

This application is a continuation-in-part of and claims priority to application Ser. No. 12/006,739, filed Jan. 4, 2008, which claims the benefit of priority to U.S. provisional application Ser. No. 60/878,621, filed Jan. 4, 2007. The disclosures of each of the foregoing applications are hereby incorporated by reference in their entirety.

BACKGROUND

Ultrasound waves have been widely used in medical applications. For example, ultrasound waves have been used for diagnostic and therapeutic purposes, as well as in many industrial applications. One diagnostic use of ultrasound waves includes using ultrasonic waves to detect underlying structures in an object or a human tissue. In this procedure, an ultrasonic transducer is placed in contact with the object or tissue via a coupling medium and high frequency (1-10 MHz) ultrasonic waves are directed into the tissue. Upon contact with various underlying structures, the waves are reflected back to a receiver adjacent the transducer. By comparison of the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

In addition to diagnostic uses, ultrasonic energy can also be used for therapeutic purposes. Two therapeutic medical uses of ultrasound waves include aerosol mist production and contact physiotherapy. Aerosol mist production makes use of a nebulizer or inhaler to produce an aerosol mist for creating a humid environment and delivering drugs to the lungs. In particular, ultrasonic nebulizers operate by the passage of ultrasound waves of sufficient intensity through a liquid, the waves being directed at an air-liquid interface of the liquid at a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred over aerosol mists produced by other methods because a smaller particle size of aerosol can be obtained with the ultrasonic waves. One of the major shortcoming of inhalers and nebulizers is that the aerosol mist cannot be directed to a target area without an air stream, which decreases the efficiency of ultrasound.

Contact physiotherapy applies ultrasonic waves directly to tissue in an attempt to produce a physical change in the tissue. In conventional ultrasound physiotherapy, an ultrasonic wave contacts the tissue via a coupling medium. This direct contact, even if via a coupling medium, may be undesirable for certain medical applications, such as in the treatment of open wounds resulting from, for example, trauma, burns, and surgical interventions.

Commonly-owned U.S. Pat. No. 6,569,099 discloses an ultrasonic device and method for wound treatment, the entire content of which is incorporated herein by reference. This patent discloses, inter alia, a device that sprays liquid particles to a wound via an applicator. The liquid particles provide a medium for propagation of the ultrasonic waves. Commonly-owned U.S. patent application Ser. No. 11/473,934, the entire contents of which is incorporated herein by reference, discloses a removable applicator nozzle for an ultrasound wound therapy device. The disclosed devices and systems can be used in non-contact methods for delivering ultrasonic energy via a liquid mist.

The present invention provides an improved applicator and kits. These applicators and kits have numerous uses, for example, in methods for delivering ultrasound energy from a non-contact distance.

SUMMARY

Improvements to the applicators used to, for example, deliver ultrasound energy to patient tissue may be desired to produce a more reliable and consistent flow of liquid particles (e.g., liquid particles of a more consistent particle size) to a wound bed or site. Improvements may also be desired to minimize the setup time for operating the devices. Improvements may further be desired to provide devices and methods that can be tailored to the treatment of different types of wounds and/or wounds located in different regions of a patient's body.

The present disclosure generally relates to the field of ultrasound wound therapy devices, and more particularly relates to a removable multi-channel applicator for enabling ultrasound energy (with or without a fluid) to be sprayed towards a patient, thus providing a medium for ultrasonic waves to travel to patient tissue where the ultrasound energy acts at the tissue surface and/or penetrates the tissue to a beneficial depth to provide anti-bacterial and/or other therapeutic effects. Without being bound by theory, the beneficial properties of the ultrasonic energy and/or fluid may be due to action of the fluid and/or energy on the surface of the wound and/or due to effects of the fluid and/or energy following penetration of the tissue to a beneficial depth.

According to one aspect, the present disclosure provides a removable multi-channel applicator. The applicator is engageable with an ultrasound therapy device and can be used, for example, to deliver ultrasound energy to patient tissue. For example, the applicator can be used with a low frequency ultrasound therapy device in the treatment of wounds.

In a first aspect, the disclosure provides an applicator, comprising a nozzle body. The nozzle body includes a plurality of channels, each channel having an inlet and an outlet. The applicator also includes a nozzle liner having an interior and an exterior surface and being engageable with the nozzle body. The applicator also includes an opening sized and shaped for introducing fluid to the inlets of the plurality of channels. In certain embodiments, the applicator includes a passageway defined by a space between the nozzle body and the nozzle liner.

In certain embodiments, the opening is sized and shaped for introducing fluid to the inlets of the plurality of channels through the passageway. In certain embodiments, the opening is a connector extending from an exterior surface of the nozzle body to an opening on an interior surface of the nozzle body. The connector can permit fluid to flow through the connector into the passageway. In other embodiments, the opening comprises a connection port extending from the nozzle liner.

In certain embodiments, the inlet of at least one of the plurality of channels has a diameter that is larger than a diameter of the outlet of said channel. In other embodiments, the inlet of at least one of the plurality of channels has a diameter approximately equal to a diameter of the outlet of said channel.

In certain embodiments, at least one of the plurality of channels extends distally following a straight line along the nozzle body. In certain embodiments, at least one of the plurality of channels is arranged in a spiral winding fashion about the center axis of the nozzle body.

In certain embodiments, the plurality of channels is on the interior surface of the nozzle body. In certain embodiments, all or a portion of the plurality of channels extends to the exterior surface of the nozzle body.

In certain embodiments, the applicator is sized and shaped for use in treating wounds with an ultrasound therapy device. For example, the applicator is sized and shaped to interconnect with a transducer assembly, which in turn can interconnect to a generator for operating an ultrasound therapy device. In operation, the applicator is interconnected to the transducer assembly so as to shield the transducer tip portion of the ultrasound transducer. In this way, the applicator provides a safety mechanism for preventing inadvertent contact with the transducer tip portion of the ultrasound transducer. Additionally, as detailed herein, the applicator facilitates delivery of ultrasound energy to patient tissue. When ultrasound energy is delivered "wet", the applicator also facilitates (i) delivery of liquid to the transducer tip portion of the ultrasound transducer and (ii) subsequent delivery of liquid spray to a surface. Accordingly, in a related aspect, the invention provides a transducer assembly interconnected to an applicator.

In certain embodiments, the subject applicators are used "wet" to deliver fluid to a transducer tip portion of an ultrasound transducer. The relative position of the transducer tip portion and the applicator can be readily modulated such that fluid is initially delivered from the applicator to any location along the length and/or circumference of the transducer tip portion (initial contact relative to a drop of fluid first contacting the transducer tip portion). Moreover, in certain embodiments, the multi-channel applicators of the invention are used to deliver fluid to a plurality of locations along the length and/or circumference of the transducer tip portion of the ultrasound transducer. After fluid has initially contacted the transducer tip portion (which in operation is vibrating at a frequency), ultrasound energy and a fluid mist ultimately emanate from the distal end of the transducer tip portion and from the distal end of the applicator. In this way, the applicator is used both to deliver fluid to the transducer tip portion and to facilitate delivery of ultrasound energy and a fluid spray to patient tissue.

In certain embodiments, the nozzle liner further includes a cover, and the opening protrudes from the cover. In other embodiments, the applicator further includes a space created when a horizontal portion of the cover of the nozzle liner is positioned against the nozzle body.

In certain embodiments, the nozzle body further includes a groove for receiving the fluid from the opening, whereby the fluid flows through the groove into the space created by the cover of the nozzle liner and the nozzle body.

In certain embodiments, the applicator further comprises a nozzle face, wherein the nozzle face comprises a proximal portion engageable with a distal opening of the nozzle. In certain embodiments, the nozzle face includes a proximal portion and a distal portion, wherein the diameter of the proximal portion is smaller than the diameter of the distal portion, In other embodiments, the nozzle face includes a proximal portion and a distal portion, wherein the diameter of the proximal portion is larger than the diameter of the distal portion.

When used in operation with an ultrasound therapy device, in certain embodiments, a fluid is pressurized to flow, through the opening, through the plurality of channels, and onto a plurality of sections of a transducer tip portion of the ultrasound wound therapy device. In certain embodiments, the opening comprises a connector, and a fluid is pressurized to flow through the connector, through an opening of the connector, through the plurality of channels, and onto a plurality of sections of a transducer tip portion of the ultrasound wound therapy device. In other embodiments, the opening comprises a connection port, and fluid is pressurized to flow through the connection port, through the plurality of channels, and onto a plurality of sections of a transducer tip portion of the ultrasound wound therapy device. The fluid may be stored in a fluid source (e.g., container), for example a bag, cartridge, canister, or bottle, and is coupled to the connector via a flexible tubing or other conduit. In certain embodiments, the fluid container is physically separate from the device and interconnected with the transducer assembly or applicator only via flexible tubing or other flexible or rigid conduit. In other embodiments, the fluid container is physically connected to the transducer assembly and/or applicator by something other than just flexible tubing. In still other embodiments, the flexible tubing is coupled to the applicator via an opening, for example via the connector, but is also connected or affixed to the applicator or to the transducer assembly at one or more additional points. In still other embodiments, the fluid container is housed within all or a portion of a generator. When housed within all or a portion of the generator, the generator optionally contains a peristaltic pump or other mechanism for modulating the delivery of fluid from the fluid container to the applicator and/or transducer assembly. In still other embodiments, the fluid container is housed within all or a portion of the transducer assembly. For example, the transducer assembly may include a fluid cartridge or canister.

The use of a pressurized system for providing fluid to an opening in the applicator (rather than a gravity-dependent fluid flow system) permits movement of the nozzle body relative to the fluid source without disturbing the fluid flow rate or particle size. For example, the use of a pressurized fluid flow system allows the operator of the wound therapy device to hold the device at any angle relative to the fluid source. Similarly, the fluid source and/or connector portion may be placed at any angle or location relative to a longitudinal axis defined by the nozzle body. This substantially increases the range of wounds and patients that can be successfully treated (e.g., patients with wounds in difficult to access places, patients with restricted mobility). Further, this permits the design and use of lower profile, more streamlined devices and nozzles.

For the foregoing reasons, the use of a pressurized system for providing fluid to an opening in the applicator is preferred. However, in other embodiments, a gravity-dependent fluid delivery system is used to deliver fluid to the applicator described herein. Gravity-dependent fluid delivery systems, for example, the systems described in U.S. patent application Ser. No. 11/473,934, filed Jun. 23, 2006, can be readily adapted for use with the improved applicator nozzle described herein.

In other embodiments, the applicator is used to deliver ultrasound energy without a liquid spray or other coupling medium. When used in this manner, fluid is not delivered to the transducer, and thus it is immaterial whether the device is otherwise configured for gravity-fed or pressurized fluid delivery.

When used with an ultrasound wound therapy device, it is envisioned that the transducer tip portion of the ultrasound wound therapy device extends between the distal opening of the nozzle liner and the distal opening of the nozzle body, and that fluid flows through the channels and contacts a plurality of sections around a circumference of the transducer tip portion. In a preferred embodiment, a separation distance from a distal end of the transducer tip portion of the ultrasound wound therapy device to the distal opening of the nozzle body is at most equal to about 0.05 inches or at most equal to about 0.06 inches. In another preferred embodiment, a separation distance from the distal opening of the nozzle liner to the distal end of the transducer tip portion of the ultrasound wound therapy device is between about 0.03 inches and about 0.09 inches or between about –0.065 inches and about 0.09 inches. However, other separation distances are possible and are within the scope of the present disclosure.

In certain embodiments, it is envisioned that an applicator is provided that includes the removable multi-channel nozzle of the present disclosure and a nozzle face. This nozzle face has a proximal portion that is configured to engage with the distal end or distal opening of the nozzle. In one embodiment, the nozzle face is a parabolic energy reflector having a proximal portion and a distal portion, wherein the diameter of the proximal portion of the energy reflector is substantially smaller than the diameter of the distal portion. Without being bound by theory, this parabolic energy collector may aid in creating and/or maintaining a standing ultrasound wave pattern between the applicator and a surface of an object, for example a surface of a wound to be treated. Additionally or alternatively, the nozzle face may be sized and shaped to facilitate treatment of particular types of wounds or wounds in a particular location of a patient's body. In an alternative embodiment, the nozzle face has a proximal portion and a distal portion, wherein the diameter of the proximal portion of the nozzle face is substantially larger than the diameter of the distal portion. Such nozzle face configurations may be particularly useful for delivering ultrasound energy and/or liquid spray to an orifice, to an interior region of a patient, or to another difficult to access surface or interior region of a patient. When a nozzle face is used, the nozzle face can be interfitted to the applicator nozzle or the nozzle face and applicator nozzle can be machined as a single component. For example, the nozzle face can be interfitted to the nozzle body.

It is envisioned that at least one of the nozzle and the nozzle face (when provided) is designed for use with a single patient. In certain embodiments, the applicator comprises means to prevent re-use of all or a portion of the applicator. In addition, at least one of the nozzle and the nozzle face is disposable. In certain embodiments, at least one of the nozzle and the nozzle face are reusable and can be cleaned and/or re-sterilized between uses.

In another aspect, the invention provides an applicator for use in treating a wound. The applicator comprises a nozzle body including a plurality of channels, each channel having an inlet and an outlet; and an opening sized and shaped for introducing fluid to the inlets of the plurality of channels. In other words, in certain embodiments, the applicator does not include a nozzle liner. In certain embodiments, when a nozzle liner is not included, it is envisioned that all or a portion of the plurality of channels extends to the exterior of the nozzle body.

In another aspect, the invention provides a kit. In certain embodiments, the kit comprises an applicator and a fluid container, optionally containing a fluid. In other embodiments, the kit comprises an applicator and flexible or rigid tubing, and optionally comprises a fluid container (with or without a fluid). Kits may also include one or more of sterile wipes, directions for use, and a warning reminding the user that the nozzle is intended for use with a single patient. The applicator is an applicator according to the present invention. For example, the applicator includes a nozzle engageable with a portion of an ultrasound wound therapy device. In certain embodiments, the kit further includes one or more interchangeable nozzle faces each engageable with a portion of the nozzle.

In another aspect, the invention provides methods for treating patient tissue from a non-contact distance. For example, an applicator, as described herein, is interconnected to an ultrasound transducer assembly and used to deliver ultrasound energy (with or without a liquid spray) to patient tissue. In certain embodiments, the method for treating patient tissue is a method for treating a wound from a non-contact distance. In certain embodiments, the ultrasound energy is low frequency ultrasound energy. In certain embodiments, the method comprises delivering ultrasound energy and a liquid spray. In other embodiments, the method comprises delivering ultrasound energy alone and in the absence of a liquid spray or coupling medium.

In certain embodiments, the method for treating patients is a method for delivering ultrasound energy without direct contact with the treated patient tissue. The method comprises providing a system for delivering ultrasound energy (e.g., a generator operably connected to a transducer assembly which is interconnected to an applicator). An effective amount of ultrasound energy, in the presence or absence of a liquid spray, is delivered from a non-contact distance to patient tissue. The delivered ultrasound energy and, where present, liquid spray has a therapeutic effect on patient tissue. For example, in the case of wound treatment, the delivered ultrasound energy has an effect on the surface of the wound and also penetrates the wound tissue. Without being bound by theory, the therapeutic effects may be due to effects of the ultrasound energy at the wound surface and/or at a depth beneath the wound surface. In certain embodiments, the therapeutic effect is selected from one or more of: decrease bacteria, kill bacteria, decrease or prevent biofilm formation, promote wound healing, and promote wound cleansing.

In another aspect, the invention provides a multi-channel applicator for delivering fluid to a plurality of sections along a transducer tip portion of an ultrasound transducer. Specifically, although the relative position of the transducer tip portion and the applicator can be readily modulated such that fluid is initially delivered from the applicator at any location along the length and/or circumference of the transducer tip portion (initial contact relative to drops of fluid first flowing, dripping, wicking, or otherwise transiting from a fluid source to contact the transducer tip portion), the multi-channel applicators of the invention are used, in certain embodiments, to deliver (e.g., to transfer from a fluid source to the transducer tip portion) fluid to a plurality of locations along the length and/or circumference of the transducer tip portion of the ultrasound transducer. After fluid has initially contacted the transducer tip portion (which in operation is vibrating at a frequency), ultrasound energy and a fluid mist ultimately emanate from the distal end of the transducer tip portion and from the distal end of the applicator. In this way, the applicator is used both to deliver fluid to the transducer tip portion and to facilitate delivery of ultrasound energy and a fluid spray to patient tissue.

In certain embodiments, the multi-channel applicator comprises any one or more of the features of the applicators described herein.

In another aspect, the invention provides a method for delivering fluid from a fluid source to a plurality of sections of a transducer tip portion of an ultrasound transducer. For example, the method comprises providing a fluid source in fluid communication with a multi-channel applicator nozzle (e.g., an applicator comprising any one or more of the features of the applicators described herein), wherein the applicator is interconnected to a transducer assembly. Fluid is provided from the fluid source to the channels of the applicator nozzle such that fluid flows from the channels to initially contact the transducer tip portion along a plurality of sections of the transducer tip portion.

Combinations of any of the foregoing aspects and embodiments of the disclosure are contemplated.

DESCRIPTION OF THE DRAWINGS

The above and other aspects, features, and advantages of the present disclosure will become more apparent in light of the following detailed description when taken in conjunction with the accompanying drawings in which:

FIG. 2d presents a cross sectional view of a removable multi-channel applicator of an alternative embodiment.

FIG. 5 presents a perspective view of a removable multi-channel applicator nozzle of another alternative embodiment.

FIG. 7c-d present perspective views of fluid flow pathways of the removable multi-channel applicator shown in FIG. 7b.

FIG. 9b presents a cross-sectional view of a portion of the removable multi-channel applicator shown in FIG. 9a.

DETAILED DESCRIPTION OF THE INVENTION

Figure 1A:
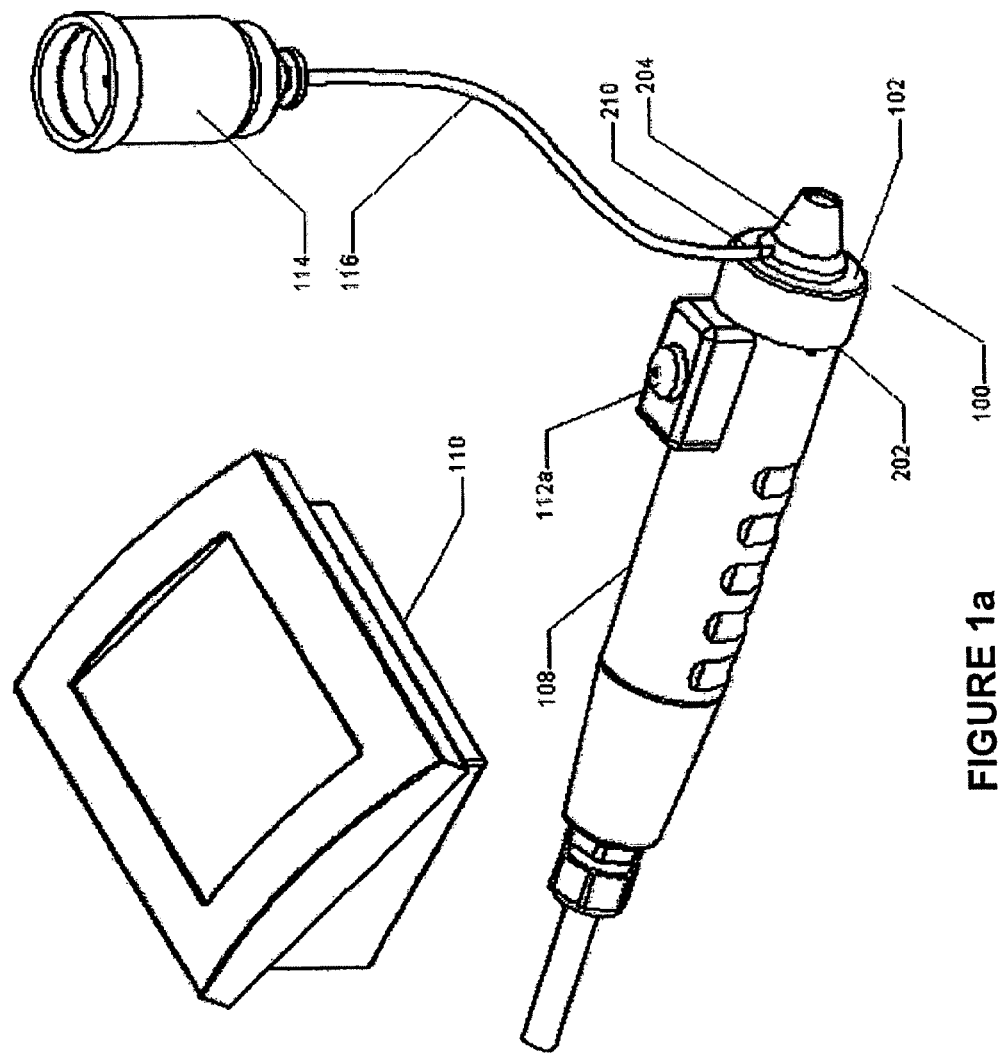
FIG. 1a presents a perspective view of a removable multi-channel applicator of the present disclosure including an applicator nozzle. The nozzle is depicted as operatively attached to a transducer of an ultrasound wound therapy device and with a fluid container coupled thereto.

Embodiments of the presently disclosed removable multi-channel applicator nozzle will now be described in detail with reference to the drawing figures wherein like reference numerals identify similar or identical elements. As used herein and as is tradition, the term "distal" refers to that portion which is farthest from the operator while the term "proximal" refers to that portion which is closest to the operator. Of note, the term "distal" also refers to that portion which is closest to the patient or other surface being treated. Further, as used herein, the word "wound" refers to surface wounds, such as burns and skin lesions; internal wounds, such as ulcers and surgical cuts due to surgery; surgical incisions; injuries, including broken bones; and other conditions or applications requiring treatment using ultrasound wound therapy.

Low frequency, non-contact ultrasound has been used in the treatment of wounds. U.S. Pat. No. 6,569,099, hereby incorporated by reference in its entirety, describes the use of ultrasound in wound therapy. Co-pending U.S. application Ser. No. 11/473,934 describes particular transducer and applicator designs, and provides further description for using non-contact ultrasound in the treatment of wounds. The present disclosure describes additional applicator and nozzle designs and kits that can be used, for example, in non-contact ultrasound therapy. For example, these applicators and nozzle designs can be used with existing or modified transducer assemblies as part of systems and methods for treating wounds using non-contact ultrasound. Additionally, however, the applicators and nozzles described herein may be interconnected with other devices intended to efficiently and effectively deliver fluid and/or ultrasound energy.

As used herein, the term "applicator" is used to refer to an applicator nozzle (also referred to as a nozzle). When a nozzle face is interconnected to an applicator nozzle, the term "applicator" refers to the interconnected unit of an applicator nozzle and nozzle face. Thus, in embodiments where a nozzle face is not interconnected to an applicator nozzle, the terms "applicator", "nozzle", and "applicator nozzle" are synonymous and can be used interchangeably. The term "nozzle" or "applicator nozzle" is used to refer to a nozzle body comprising a plurality of channels combined with one or more of a nozzle liner; a passageway defined by a space between the nozzle body and the nozzle liner; and an opening for introducing fluid to the plurality of channels. Thus, for example, in certain embodiments, the "nozzle" comprises a nozzle body comprising a plurality of channels and an opening for introducing fluid to the plurality of channels. In other embodiments, the "nozzle" comprises a nozzle body comprising a plurality of channels; a nozzle liner; and an opening for introducing fluid to the plurality of channels. In still other embodiments, the "nozzle" comprises a nozzle body comprising a plurality of channels; a nozzle liner; a passageway defined by a space between the nozzle body and the nozzle liner; and an opening for introducing fluid to the plurality of channels.

In certain embodiments, an applicator, as described herein, is interconnected with an ultrasound wound therapy device and used to deliver ultrasound energy (in the presence or absence of a liquid spray) to patient tissue. When used in this manner, the ultrasound energy (and liquid spray, if present) is delivered without contact between the applicator and the patient tissue being treated. In other words, the ultrasound energy (and liquid spray, if present) are delivered from a non-contact distance. Once delivered, the ultrasound energy penetrates the treated tissue to provide a therapeutic effect.

In certain embodiments, the ultrasound energy delivered is low frequency ultrasound energy. In certain embodiments, the ultrasound energy delivered is low intensity.

In certain embodiments, low frequency ultrasound is delivered (in the presence or absence of a liquid spray) from a non-contact distance and without causing a substantial increase in the temperature of the treated tissue.

For the treatment of certain conditions, it may be preferable to have treatment conducted in a hospital or doctor's office so that a health care professional can monitor the duration and course of the treatment. Under certain circumstances, however, it may be preferable to allow the patient to be treated at home—either by a visiting health professional or by the patient himself.

By "treating" is meant to include decreasing or eliminating one or more symptoms of a condition or disorder. When used in conjunction with an ultrasound device, low frequency ultrasound energy is administered (with or without a liquid spray) to effected tissue of a patient in need thereof. The low frequency ultrasound energy is administered without contact between the effected tissue and the ultrasound transducer or other components of the device (non-contact distance). The low frequency ultrasound energy penetrates the tissue to provide a therapeutic effect. Regardless of the mechanism of action of the ultrasound energy, these methods can be effectively used to treat patients.

Ultrasound energy can be delivered alone. Such methods are often referred to as delivering ultrasound "dry". In other words, in certain embodiments, the method comprises delivering low frequency ultrasound alone (from a non-contact distance) and in the absence of a liquid spray or other coupling agent. When used in this way, the ultrasound energy penetrates, for example, the tissue to provide a therapeutic effect. Over one or more treatments, improvement in a patient's condition can be observed. In certain embodiments, the ultrasound energy is low frequency ultrasound energy.

In other embodiments, ultrasound energy can be delivered via a liquid spray. Such methods are often referred to as delivering low frequency ultrasound "wet". In other words, a combination of ultrasound energy and a liquid spray is delivered (from a non-contact distance) to the tissue. The energy, and to some extent the liquid spray, penetrate the tissue to provide a therapeutic effect. Exemplary liquids that can be used to generate a liquid spray include saline or water. Alternatively, the liquids used to generate the spray can themselves be (or contain) a therapeutic agent, such as an antibiotic, analgesic, antiseptic, and the like. In certain embodiments, the ultrasound energy is low frequency ultrasound energy.

In certain embodiments, the method comprises very local delivery of ultrasound energy (in the presence or absence of a liquid spray) to effected tissue. In other words, the goal is to treat, to the extent possible, only effected tissue and not asymptomatic tissue. In other embodiments, the method comprises local delivery that includes effected tissue, as well as adjacent tissue—even if such adjacent tissue is asymptomatic. The patient's health professional can select the appropriate treatment approach, including the number of treatments, the duration of each treatment, and whether the treatment should be "dry" or "wet".

In certain embodiments, the method of delivering ultrasound energy (whether "wet" or "dry") using the systems and applicators provided herein is used as part of a therapeutic regimen combining one or more additional treatment modalities. Exemplary additional modalities include, but are not limited to, negative pressure therapy, topical anti-bacterial ointments, systemic antibiotics, silver-based creams, and dressings. Furthermore, the methods of the present invention may be used in combination with physical therapy, occupational therapy, psychological therapy, diet, and exercise. When used as part of a therapeutic regimen, the various treatment modalities can be administered/used a single time or multiple times and can be administered/used prior to, following, or during delivery of ultrasound energy. In certain embodiments, the one or more additional treatment modalities comprises applying a topical medicament to the patient (e.g., to the wound or surface to be treated) prior to and/or following delivering said ultrasound energy to the wound or surface to be treated.

In certain embodiments, the method for treating a patient, for example a patient with a wound, comprises a single treatment. In certain embodiments, the method for treating a patient, for example a patient with a wound, comprises multiple treatments. For example, patients may receive doses of ultrasound two or more times per week (e.g., 2, 3, 4, 5, 6, 7 times per week), for one, two, three, four, or more than four weeks. The appropriate number of treatments, and the duration of each treatment, can be determined by a health care provider based on, for example, the particular condition being treated, the severity of the condition, and the overall health of the patient. Furthermore, the health care provider can determine whether treatment should be "wet" or "dry".

In certain embodiments, the low frequency ultrasound energy delivered is approximately 10-100 kHz, approximately 20-80 kHz, approximately 20-40 kHz, approximately 35-60 kHz, or approximately, 40-50 kHz. Stated another way, for any of the foregoing or following aspects and embodiments, the invention contemplates delivering low frequency ultrasound energy. The frequency refers to the frequency at which the transducer tip portion of the ultrasound transducer vibrates. In certain embodiments, the ultrasound energy is delivered at a frequency of approximately 10-100 kHz, approximately 20-80 kHz, approximately 20-40 kHz, approximately 35-60 kHz, or approximately, 40-50 kHz. In still other embodiments, the ultrasound energy is delivered at a frequency of approximately 30-35 kHz, approximately 35-40 kHz, or approximately 40-45 kHz. In certain embodiments, the ultrasound energy is delivered at a frequency of approximately 40 kHz.

In certain embodiments, the low frequency ultrasound energy is also low intensity ultrasound energy. Intensity refers to the amount of energy transferred to the tissue. In certain embodiments, the low frequency, low intensity energy has an intensity of approximately 0.1 to 2.2 W/cm$^2$. Stated another way, in certain embodiments, the invention contemplates delivering low frequency ultrasound energy so as to provide a certain energy level to patient tissue. In certain embodiments, the ultrasound energy level provided to patient tissue is approximately 0.1-1.0 watts/cm$^2$. In certain other embodiments, the ultrasound energy level provided to patient tissue is approximately 0.1-0.7 watts/cm$^2$.

In certain embodiments, non-contact distance between the distal most surface of the applicator (either the distal most end of the nozzle or, when present, the distal most end of the nozzle face) and the tissue or surface being treated is a non-contact distance of at least 0.1 inches (2.5 mm). In other embodiments, the non-contact distance is from about 2.5 mm to about 51 cm. In other embodiments, the non-contact distance is from about 15 mm to about 25 mm. Regardless of the exact distance, non-contact treatment means that there is no contact between the applicator and the effected tissue or surface that is being treated. It should be noted that non-contact refers to the absence of contact with the tissue or surface that is being treated. However, in certain embodiments, it is possible that components of the applicator or device may contact the tissue or surface that is not being subjected to treatment. For example, to facilitate delivery of the ultrasound energy, a handle of the device may be affixed to a patient's arm, thereby alleviating the need for an operator to hold the device throughout treatment. Such contact with other patient tissue that is not being subjected to treatment does not alter the characterization of the treatment as "non-contact".

In certain embodiments, the low frequency ultrasound energy does not significantly decrease the viability of human cells of the effected tissue. In certain embodiments, the low frequency ultrasound energy delivered from a non-contact distance via the subject applicators is non-thermal. In other words, delivery of the ultrasound energy (and optionally liquid spray) does not cause a significant increase in the temperature of the treated patient tissue (e.g., does not increase the temperature of the treated patient tissue by more than approximately 1° F.).

Combinations of one or more of any of the foregoing or following aspects and embodiments of the disclosure are contemplated. For example, any of the applicator designs disclosed herein can be used, for example, with an ultrasound device. For example, and as described herein, in operation with an ultrasound device, the applicator is interconnected to a transducer assembly, and the transducer assembly is operably interconnected to a generator, thereby providing an ultrasound treatment system. Prior to use "wet", the applicator is interconnected or otherwise placed in fluid communication with a fluid source. In this way, fluid is provided to the applicator and, in turn, provided to a portion of the transducer tip. Once provided to a vibrating portion of the transducer tip, ultrasound energy and a fluid spray is delivered from a distal end of the applicator. As discussed in detail herein, in certain embodiments, the applicator is chosen to deliver fluid from a fluid container to a plurality of sections of the transducer tip portion. Further, any of the applicator designs disclosed herein can be used in a therapeutic method to deliver ultrasound energy and/or a liquid spray to patient tissue.

All operable combinations of any of the aspects, embodiments, and features described herein are contemplated. Further exemplary features of the applicators are described below with reference to the figures.

Figure 1B:
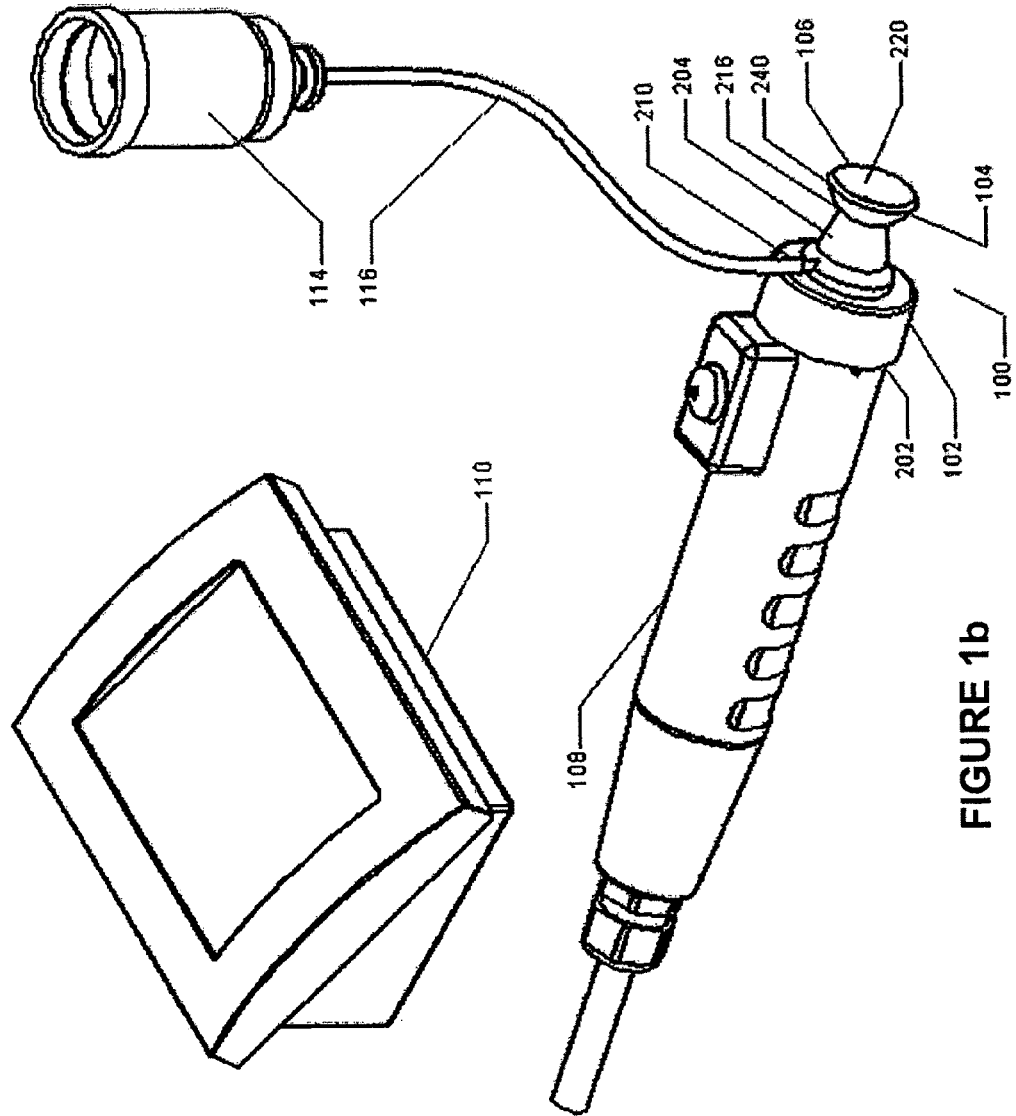
FIG. 1b presents a perspective view of the removable multi-channel applicator of an alternative embodiment including an applicator nozzle and an applicator nozzle face. The applicator is operatively attached to a transducer of an ultrasound wound therapy device and with a fluid container coupled thereto.
Figure 9A:
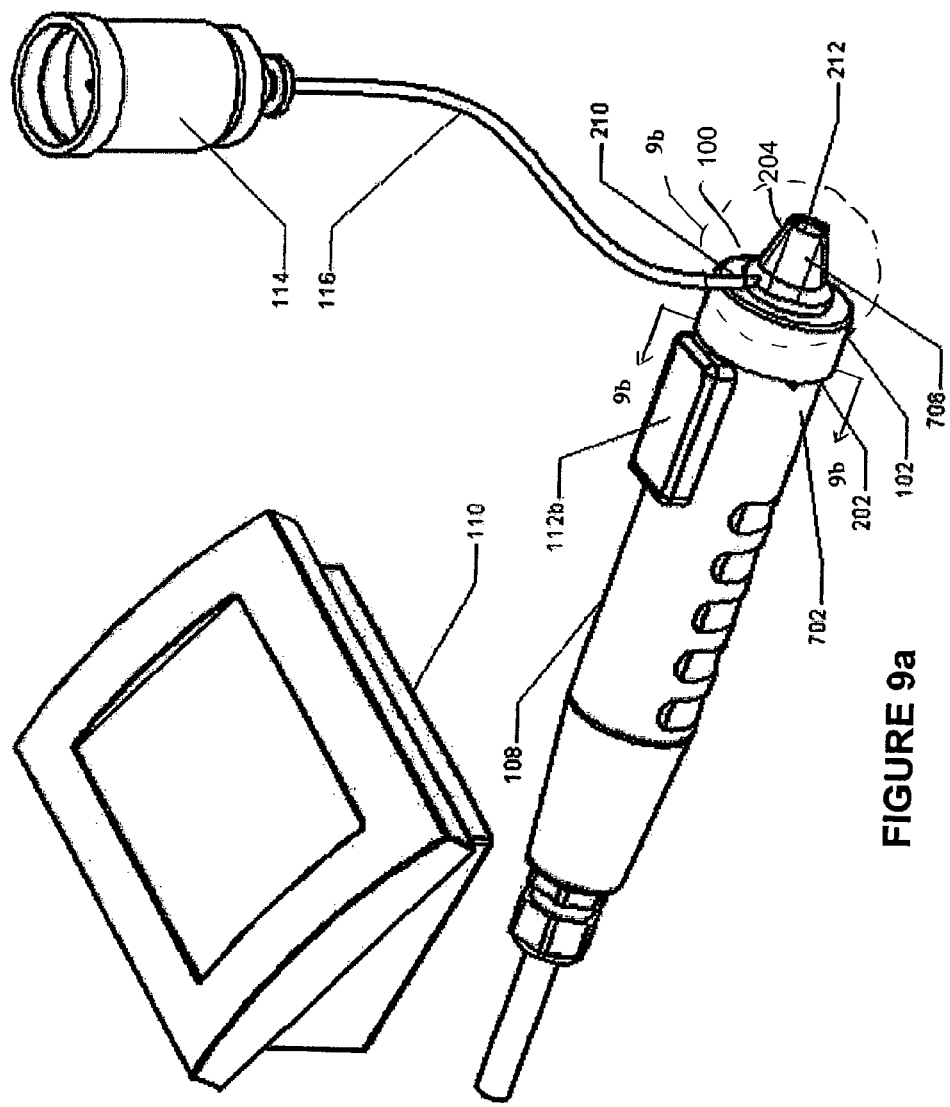
FIG. 9a presents a perspective view of a removable multi-channel applicator of an alternative embodiment operatively attached to a transducer of an ultrasound wound therapy device.
Figure 9B:
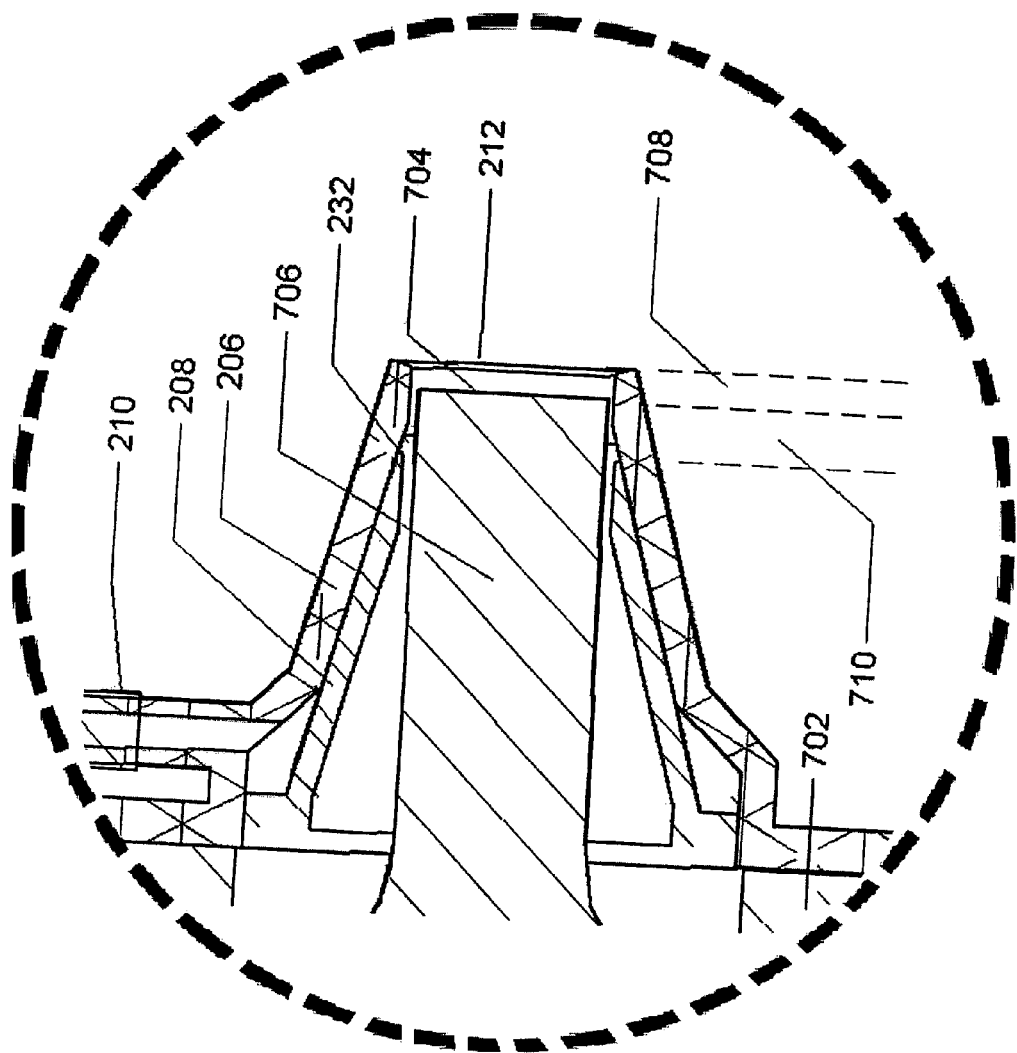

FIG. 1a illustrates, among other components, an applicator 100 having a nozzle 102 (FIGS. 2-6). In certain embodiments and as shown in FIG. 1b, the applicator 100 further includes a nozzle face 104 (FIGS. 2c and 10a-b) that is coupled to the applicator nozzle 102. In FIGS. 2a-c, the nozzle 102 includes a proximal region 202, a distal region 204, a nozzle body 206, a nozzle liner 208, a connector 210, a distal nozzle opening 212, and a plurality of fluid channels 214. In some embodiments, the proximal region 202 of the nozzle body 206 has a larger diameter than the distal region 204, such that the nozzle body 206 has a truncated conical shape. In some embodiments, the nozzle body 206 is symmetrical about the its center axis (not shown). As depicted in, for examples FIGS. 1b and 2a-c, the applicator includes a nozzle face 104. However, applicators without a nozzle face 104 are similarly contemplated and are depicted, for example, in FIG. 1a. The nozzle face 104 includes a proximal region 216, a distal region 240, and a distal nozzle face opening 220. In alternative embodiments, shown in FIGS. 4a-b, 5, and 6a-c, nozzles 102 having different number of channels, channel shapes, and channel dimensions are provided, respectively. In other alternative embodiments, shown in FIGS. 10a-b, nozzle faces 104 having different sizes and shapes are provided. FIGS. 9a-b depict an alternate embodiment of the applicator 100 without the nozzle face 104.

In certain embodiments, it is envisioned for the applicator 100 of the present disclosure to be designed for use with an ultrasound wound therapy device, such as the device described in U.S. Pat. No. 6,569,099, the entire content of which is incorporated herein by reference. The present disclosure is also related to U.S. Pat. Nos. 6,478,754 and 6,663, 554 and U.S. patent application Ser. Nos. 09/684,044 and 11/473,934, the entire content of both patents and both patent applications is incorporated herein by reference.

Briefly, the foregoing patents and applications teach that delivery of ultrasound energy and a liquid mist to a wound, such mist generated by contacting a vibrating ultrasound transducer with drops of liquid, promotes wound healing and decreases the healing time of wounds. More specifically, liquid is delivered to a vibrating tip portion of an ultrasound transducer to generate a liquid mist. Without being bound by theory, the ultrasound energy and/or liquid mist penetrate the tissue to a beneficial depth to provide a therapeutic effect even though the energy is provided to the wound at a non-contact distance (e.g., without contact between the ultrasound transducer and the patient or wound). Additionally, and without being bound by theory, the ultrasound energy and/or liquid mist provide a therapeutic effect at the tissue surface.

The foregoing patents and applications provide various ultrasound transducers and transducer assemblies, treatment algorithms, and exemplary nozzle and fluid delivery designs. Furthermore, the foregoing patents and applications teach the delivery of numerous fluids including, but not limited to sterile water, saline solution (including sterile saline solution), antibiotics, antifungal agents, growth factors, and other medicaments. In certain preferred embodiments, the liquid consists essentially of saline solution, such as sterile saline solution. In other words, in certain preferred embodiments, saline solution that does not contain a therapeutic medicament is the liquid delivered.

The present invention provides an alternative applicator for use with the ultrasound wound therapy methods, transducers, assemblies, and other components disclosed in the foregoing patents and applications. The invention contemplates combinations of any of the aspects and embodiments of the applicator and fluid container disclosed herein with any of the aspects and embodiments of the ultrasound wound therapy methods, transducers, assemblies, and other components disclosed in the foregoing patents and applications. Additionally, the present disclosure contemplates that the applicator provided herein may be used in other methods of treating patient tissue and/or in combination with other devices or systems for delivering ultrasound and/or fluid to patient tissue.

FIGS. 1a-b illustrate an exemplary ultrasound wound therapy device having an applicator 100 connected to a transducer assembly 108, which, in turn, operatively connects to a generator 110. The generator 110 includes various components necessary to supply power to the transducer assembly 108. It is noted that, as depicted, the visible portion of the transducer assembly 108 is the plastic housing of the transducer assembly. The actual transducer, from which the transducer tip portion (the portion of the transducer contacted with fluid in operation) extends distally is not visible in these drawings. Moreover, the transducer tip portion is not visible in FIG. 1a, but can be seen in the views depicted in FIGS. 3, 9a, and 9b.

The generator 110 may also contain a graphical user interface (GUI) for displaying information helpful to the operator. The generator 110 consists of three major functional sections: the AC MAINS, the main board, and the GUI board. The AC MAINS is connected to an appliance inlet with a hospital grade detachable power cord. The appliance inlet is a power entry module listed for medical applications. In certain embodiments, the appliance inlet is a power entry module with an 115V/230V voltage selection, and is designed to operate on 115V ac and 60 Hz (e.g., for operation in North America) or 230V ac and 50 Hz (e.g., for operation in Europe).

The MAIN board converts the secondary output voltage from the MAINS transformer to the low voltage power rails for the internal electronics and the drive voltage for the drive electronics to the transducer assembly 108. The MAIN board contains a microprocessor that controls, measures, and monitors the drive electronics. The transducer assembly 108 connects to the MAIN board. The microprocessor, referred to as the engine, monitors the performance of the system and communicates the information to a second microprocessor located on the GUI board. In certain embodiments, the engine communicates to the second microprocessor via a RS-232 communication link. In certain embodiments, the electronics drive the ultrasound portion of the drive electronics with a push-pull converter that has a feedback loop with a Phase Locked Loop (PLL) to track the center frequency of the ultrasound components.

The GUI board provides the graphical user interface for the operator. A custom membrane switch panel with, for example 6 keys, allows the operator to select the functions and operating parameters of the system. A purchased graphical LCD display, connected to the GUI board, can be used to display information to the operator. For example, information about the system's status, mode of operation, and treatment time can be displayed via the GUI. The GUI may have a back light generator for the LCD on it. The GUI microprocessor runs the system by controlling the human interface and running the various algorithms to control the operation of the system. For example, a treatment algorithm can be run on the GUI microprocessor. In certain embodiments, the ultrasound wound therapy device may include one or more of a timer to record total treatment time, a timer to count-down from a selected treatment time to zero, and an alarm to indicate that the total treatment time has elapsed or that there is a problem with some component of the device.

FIG. 1a depicts an applicator 100 having a nozzle 102. In an alternative embodiment, as shown in FIG. 1b, the applicator 100 may also include a nozzle face 104 coupled to the nozzle 102 from the distal region 204 of the nozzle. Details regarding the nozzle face 104 of the applicator 100 will be described in greater detail with regard to FIGS. 10a-b. When used with an ultrasound wound therapy device, the applicator 100 mechanically engages with the transducer assembly 108 of an ultrasound wound therapy device. A proximal portion 202 of the nozzle 102 slides over a distal portion 702 of the transducer assembly 108. In certain implementations, a plurality of aligning slots (not shown) of the nozzle 102 may be provided to engage with a plurality of aligning pins (not shown) of the transducer assembly 108. Regardless of the specific means by which the proximal portion 202 of the nozzle 102 engages with the transducer assembly 108, the invention specifically contemplates that the applicator 100 is removable and can be reversibly mated to the transducer assembly. In certain embodiments, all or a portion of the applicator 100 is disposable. In other words, all or a portion of the applicator 100 is intended to be used once, and then discarded. In other embodiments, all or a portion of the applicator 100 can be sterilized following use, and re-used. For example, all or a portion of the applicator 100 can be autoclavable or gamma-irradiatable.

FIGS. 1a-b also show a switch 112a that may control one or more of the power supplied to the transducer assembly 108, the flow of fluid, or the fluid flow rate. Also shown is a fluid source 114 and tubing 116 that interconnects the fluid source 114 to the nozzle 102 via a connector 210. As depicted, the connector comprises an opening in communication with the plurality of channels in the interior of the nozzle body, such that fluid can flow from the fluid source to the plurality of channels.

Although not shown in FIGS. 1a-b, a transducer tip portion extends distally from the transducer assembly. The transducer tip portion is sometimes referred to in the literature as a horn. In operation, the transducer tip portion vibrates and emits the ultrasound energy. In certain embodiments, the nozzle is used to deliver ultrasound energy and a liquid spray. When used to deliver both ultrasound energy and a liquid spray, the vibrating tip portion of the ultrasound transducer is contacted with liquid, thereby generating a liquid spray. In certain embodiments, the applicators of the present invention are used to deliver liquid essentially simultaneously to a plurality of positions on the tip portion of the ultrasound transducer (on the transducer tip portion). The use of an applicator or other means to deliver liquid to the vibrating transducer tip portion at a plurality of positions is in contrast to previous methods where liquid was delivered to the transducer tip portion via a single initial point of contact. For example, an applicator or other mechanism to deliver liquid to the transducer tip portion via a plurality of initial points of contact is in contrast to prior designs where liquid was dripped on the transducer tip portion via a single fluid opening or flowed through an orifice in the transducer itself.

The ultrasound energy and liquid spray are then delivered to the wound via the distal nozzle opening. In certain embodiments, the nozzle is used to deliver ultrasound energy alone, in the absence of a liquid spray or coupling agent. When used "dry", the nozzle is used to deliver ultrasound energy in the absence of a liquid spray or coupling agent.

In use, the transducer tip portion is shielded by the applicator such that neither an operator nor a patient can readily contact the transducer tip portion. The entire transducer tip portion, including the distal most end, is shielded by the applicator once the applicator is interconnected to the transducer assembly (See, elements 706 and 704 of FIG. 9). In other words, the distal most portion of the transducer tip is proximal to the distal most tip of the applicator, when the applicator is interconnected to the transducer assembly. As such, one benefit of the applicator and nozzle configurations provided herein is increased patient and operator safety.

Figure 2A:
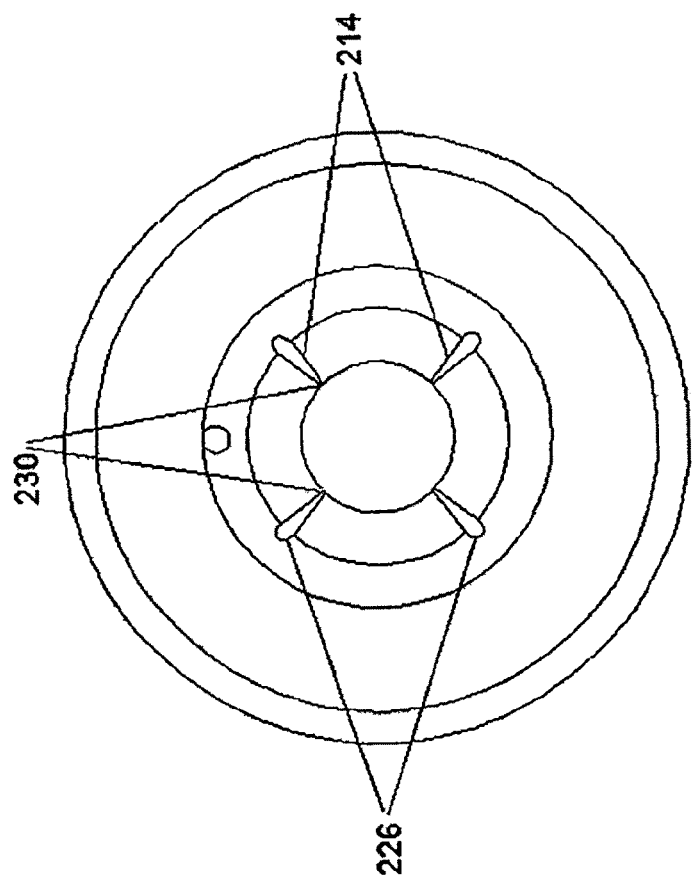
FIGS. 2a-c present an end view, a perspective view, and a profile view, respectively, of the removable multi-channel applicator of FIG. 1b.
Figure 2B:
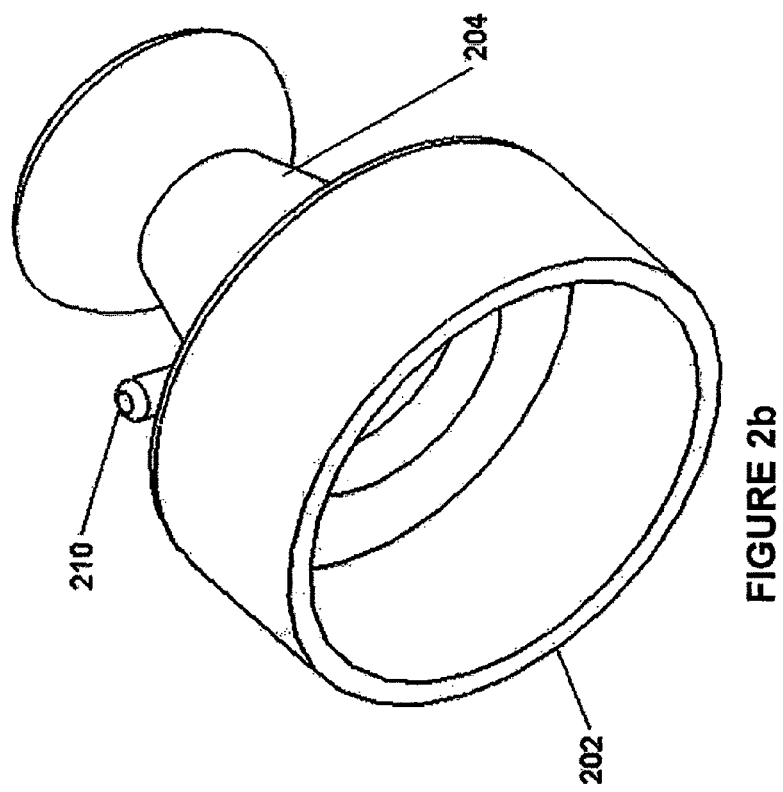
Figure 2C:
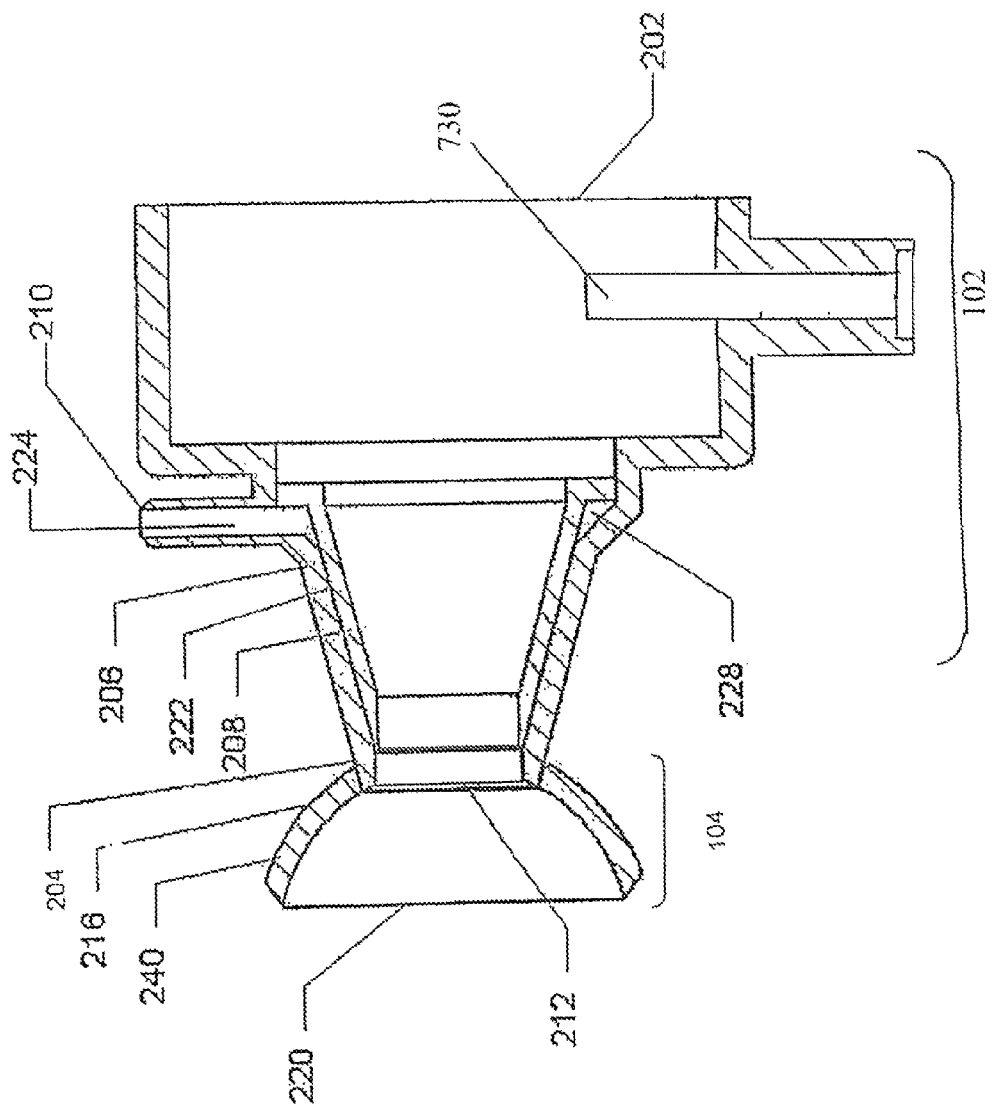
Figure 2E:
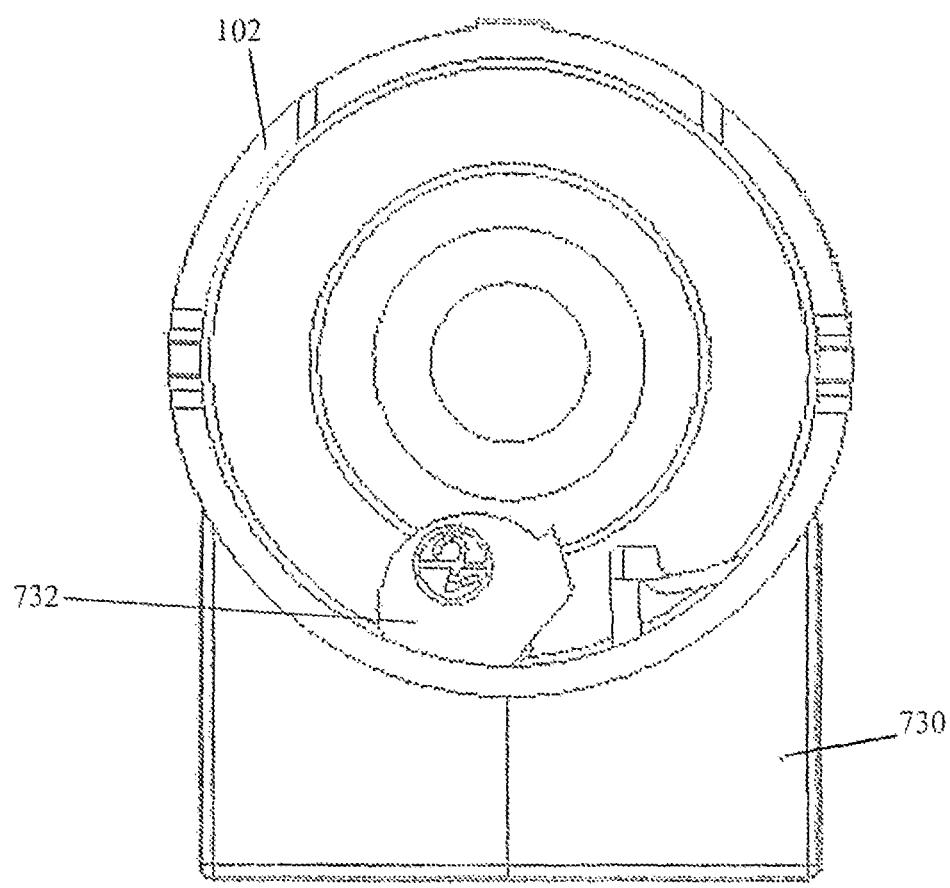
FIG. 2e depicts an end view of the removable multi-channel applicator of FIG. 1b.

FIGS. 2a-c illustrate an exemplary applicator 100 including a multi-channel applicator nozzle 102 and a nozzle face 104. The nozzle 102 includes a connector 210, a nozzle liner 208, a nozzle body 206 coaxially disposed around the nozzle liner 208, and a distal nozzle opening 212 defined by a distal end of the nozzle body 206. The nozzle 102 also includes a plurality of channels 214 in the interior surface 222 of the nozzle body 206. These channels may be injection molded in place during the manufacture of the nozzle. In some embodiments, the channels may be etched or machined. The nozzle body 206 and the nozzle liner 208 may be injection molded using thermoplastic ABS (Acrylonitrile-Butadiene-Styrene).

As depicted in FIGS. 2a-c, the connector 210 is oriented on an axis substantially perpendicular to a longitudinal axis of the nozzle 102 and is configured to permit introduction of a fluid, such as saline, into the interior of the nozzle 102. For example, the connector 210 may be sized and shaped to interconnect with a flexible or a rigid tubing or a cartridge to facilitate fluid flow from a fluid source to the connector. In particular, the connector 210 extends from the exterior of the nozzle body 206 to an opening 224 on the interior surface 222 of the nozzle body 206.

In some embodiments, the nozzle liner 208, which may have a truncated conical shape, is snap fitted to the nozzle body 206, which may also have a truncated conical shape. In certain embodiments, when the nozzle liner 208 is fitted to the nozzle body 206, a space is created between the nozzle liner 208 and the nozzle body 206. In some embodiments, a passageway 228 is defined by this space. The space is enclosed by the nozzle liner 208 and the nozzle body 206. In some embodiments, the passageway 228 has a ring shape with a triangular cross section (shown in FIG. 2C) and encircles a portion of the nozzle liner 208. In some embodiments, the opening 224 of the connector 210 opens into the passageway 228. The fluid enters the passageway 228 through the opening 224 and fills the passage 228. The tight fit created between the nozzle liner 208 and the nozzle body 206 prevents the fluid in the passageway 228 from leaking out of the passageway 228. Connector 210 is one example of a means for providing fluid from outside the nozzle body to an opening that is in fluid communication with the plurality of channels.

FIG. 2d shows a cross sectional view of the inlets 226 of the channel 214 being in contact with the passageway 228. As the pressurized fluid fills the enclosed passageway 228, the fluid flows into the multiple channels 214 through the respective inlets 226 of the channels 214.

When the fluid exits from the plurality of channels 214 via respective channel outlets 230, the fluid contacts a tip portion 706 of the transducer assembly 108 at multiple sections around a circumference of the tip portion 706. The inlets 226 and outlets 230 of the channels 214 may be appropriately sized to allow an even coating around the entire circumference of the tip portion 706. In some embodiments, the tip portion 706 of the transducer assembly 108 wicks the fluid around its circumference. In some embodiments, having a plurality of evenly spaced channels 214 around the circumference of the tip portion 706 of the transducer assembly 108 may shorten the time needed for the fluid to coat the circumference of the tip portion 706 before the transducer assembly 108 is activated. In certain embodiments, once the fluid begins to flow onto the transducer assembly 108 from the multiple channels 214 of the nozzle 102, almost no time is delayed for the fluid to fully coat the tip portion 706 of the transducer assembly 108.

Figure 3:
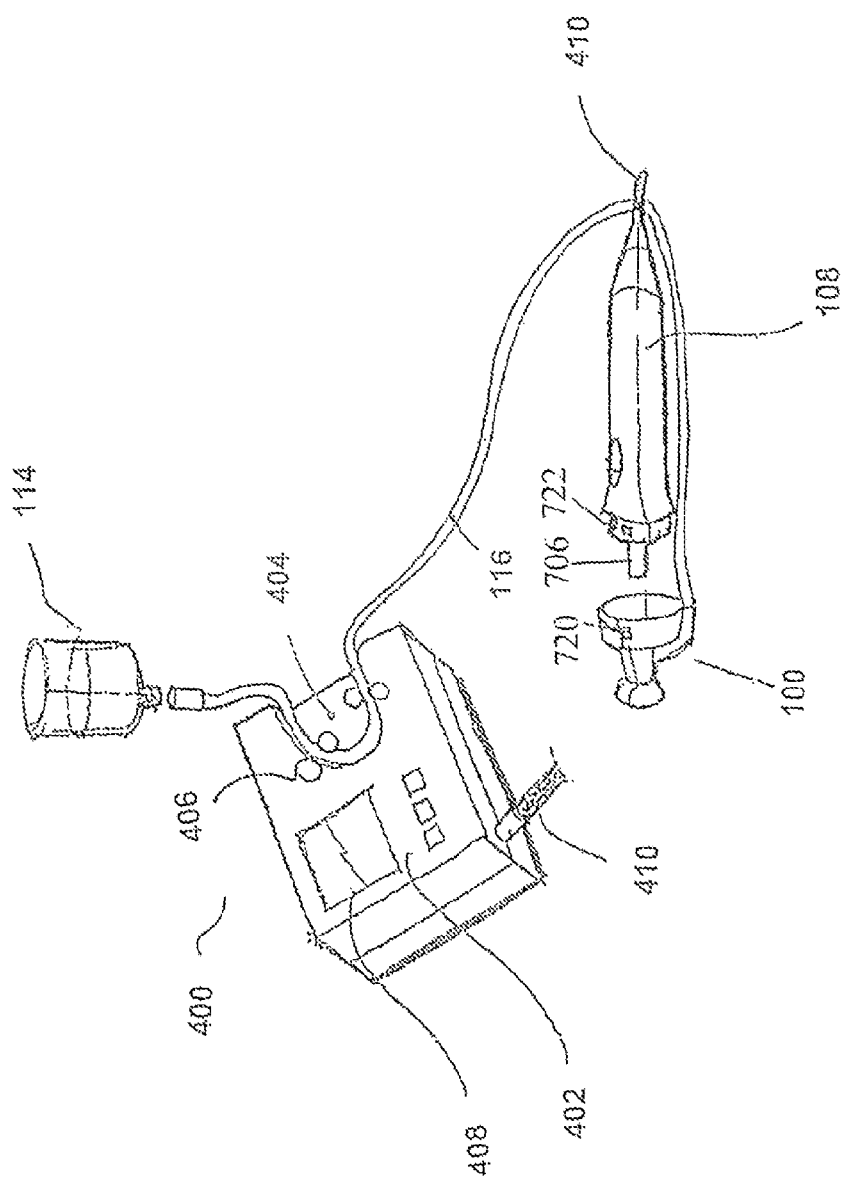
FIG. 3 presents a perspective view of a removable multi-channel applicator of the present disclosure interconnected to a generator-pump unit 400. The applicator is depicted just prior to being operatively attached to a transducer of an ultrasound wound therapy device and with a fluid container coupled thereto.

The connector 210 of the nozzle 102 is configured to receive the fluid into the interior of the nozzle 102. In certain embodiments, the fluid is pressurized to enter the nozzle 102 via the connector 210 once a user unclamps the tubing 116 that interconnects the fluid container 114 to the connector 210 or otherwise begins the flow of fluid from the fluid container 114. Such unclamping can be performed manually by the user. In some embodiments, a peristaltic pump is used. A peristaltic pump at least includes a rotor and rollers or other tube-engaging members movable within a housing relative to the clamped flexible tubing. A peristaltic pump typically includes between four to six rollers. The rollers compress the clamped flexible tubing. As the rotor turns, the part of the tube under compression gets pinched and the pinching motion forces the fluid to move through the tube. The rollers relax the clamped flexible tubing as the rotor turns and the flexible tubing opens to its original state to induce fluid flow. FIG. 3 shows a fluid container 114, a tubing 116, an applicator 100, and a generator-pump unit 400. The generator-pump unit 400 includes, among other things, a generator portion 402, a pump portion 404, multiple rollers 406, an LCD display 408, and a connection inlet 410. The generator portion 402 may automate the fluid to enter the nozzle by, for example, regulating a valve (not shown) coupled to the tubing 116. In addition, the pressure applied to the fluid may be automatically maintained by the generator 402 based on values supplied by the user from a user interface, such as a dial, coupled to the generator 402. In addition, the generator 402 may report to the user the monitored pressure readings in the LCD display 404 of the generator 402. Although not shown, the generator-pump unit 400 may include an outer cover to protect the rollers 406 and the flexible tubing. In certain embodiments, all or a portion of the flexible tubing and/or fluid container may be housed with the generator-pump unit 400, rather than provided external to the generator-pump unit 400. In certain embodiments, the generator-pump unit 400 is fully integrated such that it performs all of the functions of the generator 110 depicted in FIG. 1a.

In some embodiments, the pressurized fluid is delivered to the connector and to the nozzle at a constant flow rate regardless of the quantity of fluid in the fluid container, the angle or orientation of the transducer assembly 108 or applicator 100, or the position of the fluid container 114 relative to the transducer assembly 108. Hence, the use of a pressurized delivery system such as a peristaltic pump may allow the connector 210 to be placed at any angle or orientation relative to the nozzle 102. For example, the center axis defined by the connector may be substantially perpendicular, parallel or at an angle in relation to the longitudinal axis of the nozzle. In addition, the connector may be placed upright in relation to the transducer assembly, as depicted in FIGS. 1a and 1b, or at an angle as depicted in FIG. 3, or at any other position on the nozzle 102. The use of a pressurized delivery system allows the operator increased mobility and expands the range of wounds that can be effectively treated. Additionally, the increased mobility helps decrease operator fatigue. In some embodiments, the pressure may be similar to the pressure of the fluid under a gravity-fed condition. The pressure applied to the fluid may be influenced by the sizes and/or shapes of the channel outlets 230 (FIG. 2A).

In certain nozzle designs, the circumference of the nozzle 102 decreases distally. In other words, the diameter of the distal opening 212 of the nozzle 102 may be smaller than the diameter of the proximal portion 202 of the nozzle 102. In certain embodiments, the diameter of the distal opening 212 of the nozzle 102 is approximately 60% the diameter of the proximal portion 202. In certain embodiments, the diameter of the distal opening 212 is approximately 50%, 40%, 33%, 30%, 27.5%, or 25% the diameter of the proximal portion.

Figure 4A:
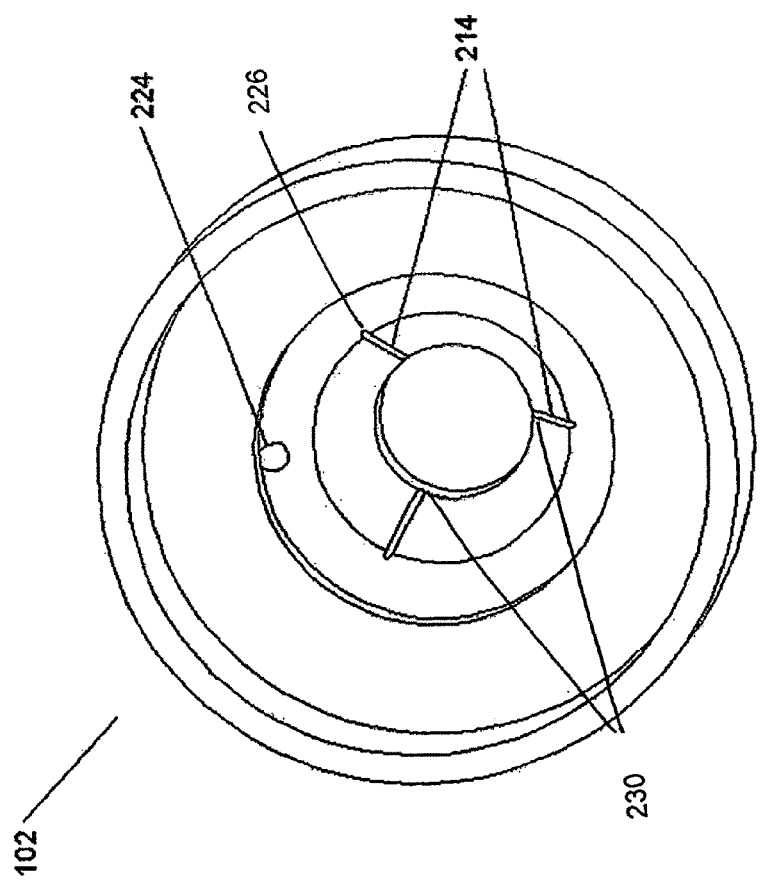
FIGS. 4a-b present perspective views of a plurality of removable multi-channel applicator nozzles of alternative embodiments.
Figure 4B:
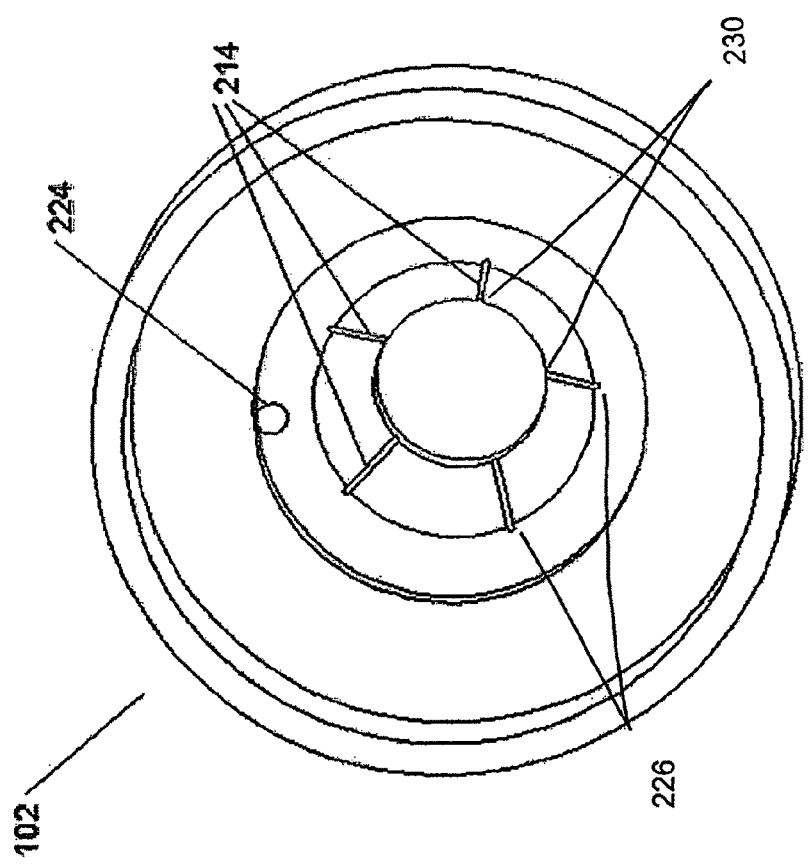

In the illustrative embodiment of FIGS. 2a-2c, four straight channels 214 are radially dispersed in the interior surface 222 of the nozzle body 206. In alternative embodiments, the nozzle body 206 has a different number of the channels. For example, FIGS. 4a-b provide exemplary nozzle structures 102 having three and five straight channels 214, respectively. It is envisioned that the channels are arranged in a radially symmetrical position with respect to the center axis of the nozzle body 206. In other embodiments, the channels 214 may be dispersed at varying distances from one another. In other words, the channels 214 are asymmetrical about the center axis of the nozzle body 206. It is also envisioned that the number of channels 214 in a nozzle 102 may affect the resulting spray pattern. For example, the three- and four-channel nozzles 102 may produce more consistent spray patterns than nozzles 102 having a higher number of channels 214. This is because a nozzle 102 having more than four channels 214 needs to be offset with a reduced fluid flow rate in each channel 214 in order to achieve a flow rate equivalent to that produced by a single-channel nozzle 102. The reduced flow rate may lead to a reduction in the quality of liquid mist formation and may increase the amount of fluid that drips from the applicator 100. However, nozzles having greater than four channels or less than three channels are also contemplated. The fluid flow rate can be appropriately adjusted based on the number of channels included in the nozzle body. In certain embodiments, the nozzle body includes 2 channels, 3 channels, 4 channels, 5 channels, or 6 channels. As noted above, the plurality of channels may be evenly spaced or asymmetrically dispersed. In certain embodiments, the plurality of channels are etched, molded, or otherwise presented on the interior surface of the nozzle body. However, it is also contemplated that all or a portion of the plurality of channels may extend or be present on an exterior surface of the nozzle body.

FIG. 5 shows the diameter of an inlet 226 of a channel 214 being larger than the diameter of an outlet 230 of the channel 214. Hence, as a fluid travels distally through the channel 214, the fluid flow tends to become increasingly restricted. In an alternative design, the cross-sectional channel size is approximately uniform throughout the entire length of the channel 214. The restriction on cross-sectional channel size may also be implemented to compensate for the usage of a pressurized system.

In certain embodiments, the nozzle body includes a plurality of channels, each of which has the same or approximately the same cross-sectional channel size. In other embodiments, at least one of the plurality of channels has a cross-sectional channel size that differs from at least one other of the plurality of channels.

Figure 6A:
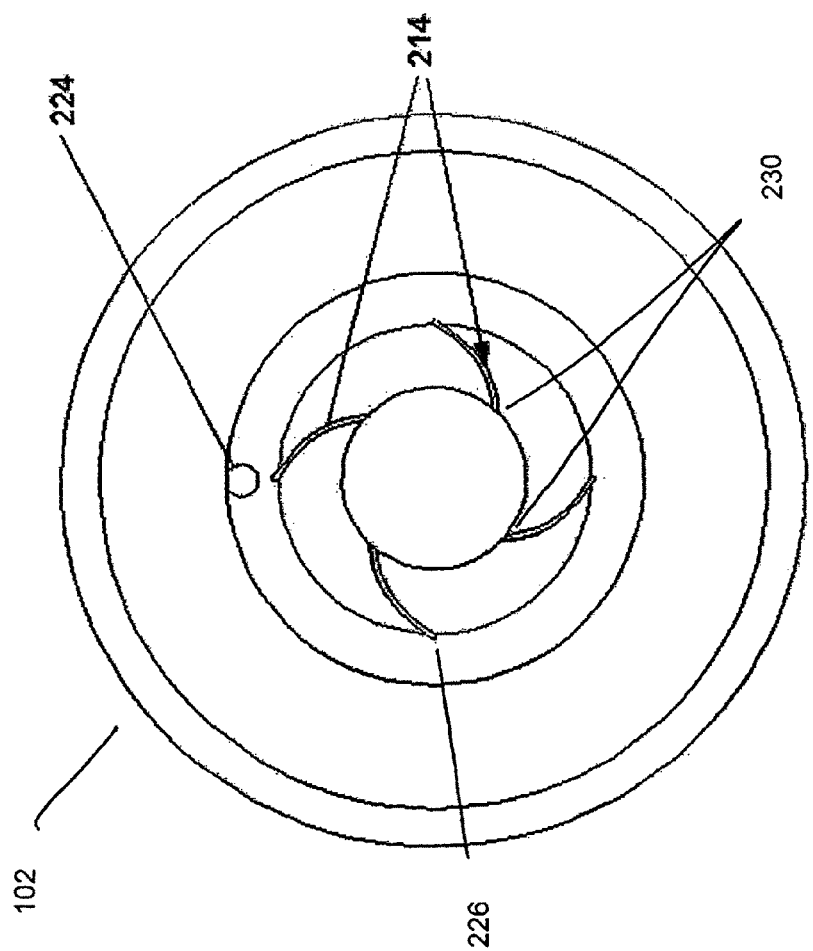
FIGS. 6a-c present an end view, a perspective view, and a profile view, respectively, of a removable multi-channel applicator nozzle of yet another alternative embodiment.
Figure 6B:
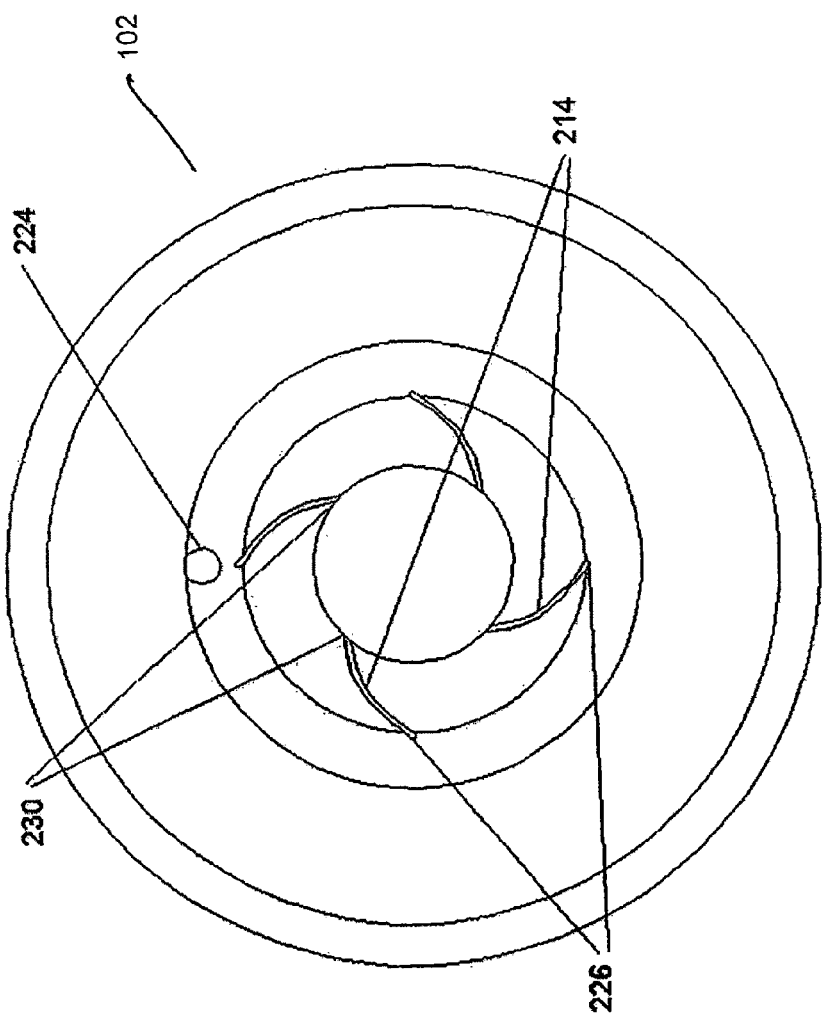
Figure 6C:
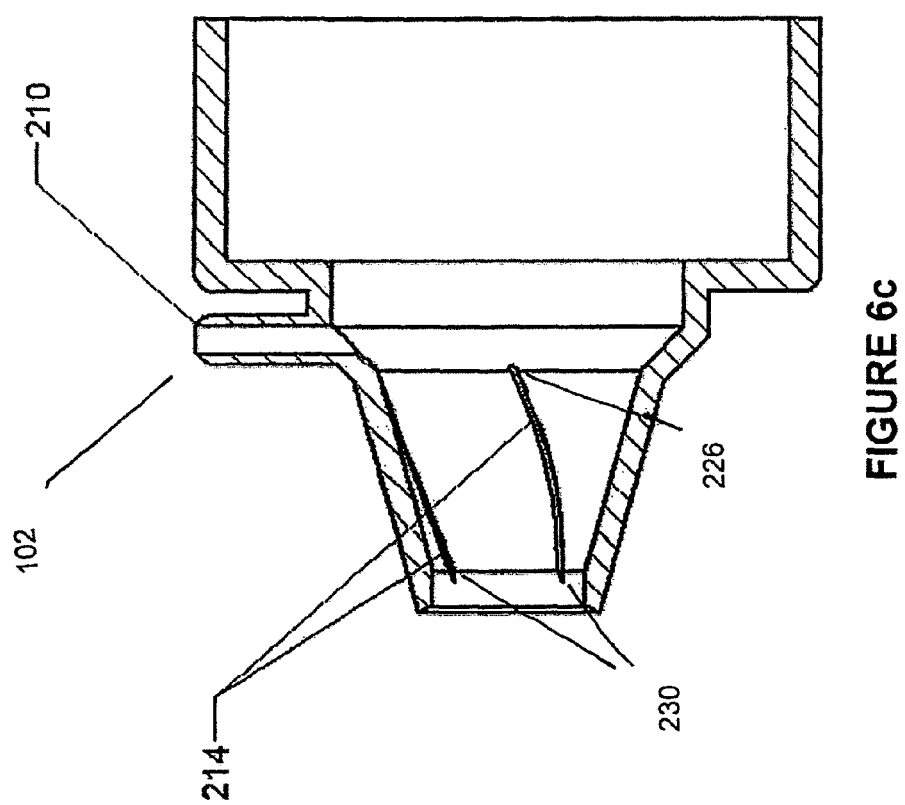

In an alternative embodiment, as shown in FIGS. 6a-c, an exemplary nozzle structure 102 having four spiral-shaped channels 214 is provided. These channels may be arranged by following a curve (not shown) on the interior surface of the nozzle body 206 that winds about the center axis (not shown) at a continuously decreasing distance from the center axis. In some embodiments, the inlets of the channels may be evenly spaced from one another. In some embodiments, the outlets of the channels may be evenly spaced from one another. However, the invention contemplates unevenly spaced inlets and/or outlets of the channels. Regardless of the number and spacing of the channels, the invention contemplates the use of channels of varying shapes and dimensions. Furthermore, the invention contemplates that the multiple channels can each be of the same shape and dimension or can be of differing shapes and/or dimensions.

The flow rate of the fluid may be controlled by the diameter of the inlets and outlets of the channels and/or the applied fluid pressure. In certain embodiments, the diameter of the inlet and the outlet of the channel may be reduced to minimize the amount of fluid that drips from the applicator 100. In such situations, the applied fluid pressure may be increased to maintain the flow rate with the reduced diameter of the channel.

In certain embodiments, it is envisioned for the diameter of the connector opening 224 of the connector 210 to be about 0.035 inches or greater. In certain embodiments, the diameter may be about 0.08 inches. It is envisioned for the diameter of the channel inlets 226 to be about 0.05 inches. In certain embodiments, the diameter of the channel outlets 230 may vary with the number of channels in the nozzle. For example, the diameter of the channel outlets 230 for the four-channel nozzle design of FIG. 2 may be about 0.01 inches. In addition, the diameters of the channel outlets 230 for the three-channel nozzle of FIG. 4a, five-channel nozzle of FIG. 4b, and six-channel nozzle (not shown) may be about 0.012 inches, 0.009 inches, and 0.008 inches, respectively. In general, the dimension of the channel outlets is inversely proportional to the number of channels in the nozzle. A combination of the aforementioned sizes for the connector opening 224, the channel inlets 226 and the channel outlets 230 may generate relatively uniform particle sizes of fluid. The particle sizes may be approximately equal to 60 μm in diameter. For example, the approximately uniform sized particles may be approximately equal to 40 μm, 45 μm, 50 μm, 55 μm, 60 μm, or 65 μm in diameter. In certain embodiments, the diameter of the distal opening 220 of the nozzle face 104 is about 1.00 inch. The foregoing measurements are exemplary, and other operable combinations of sizes and shapes are similarly contemplated.

Figure 7A:
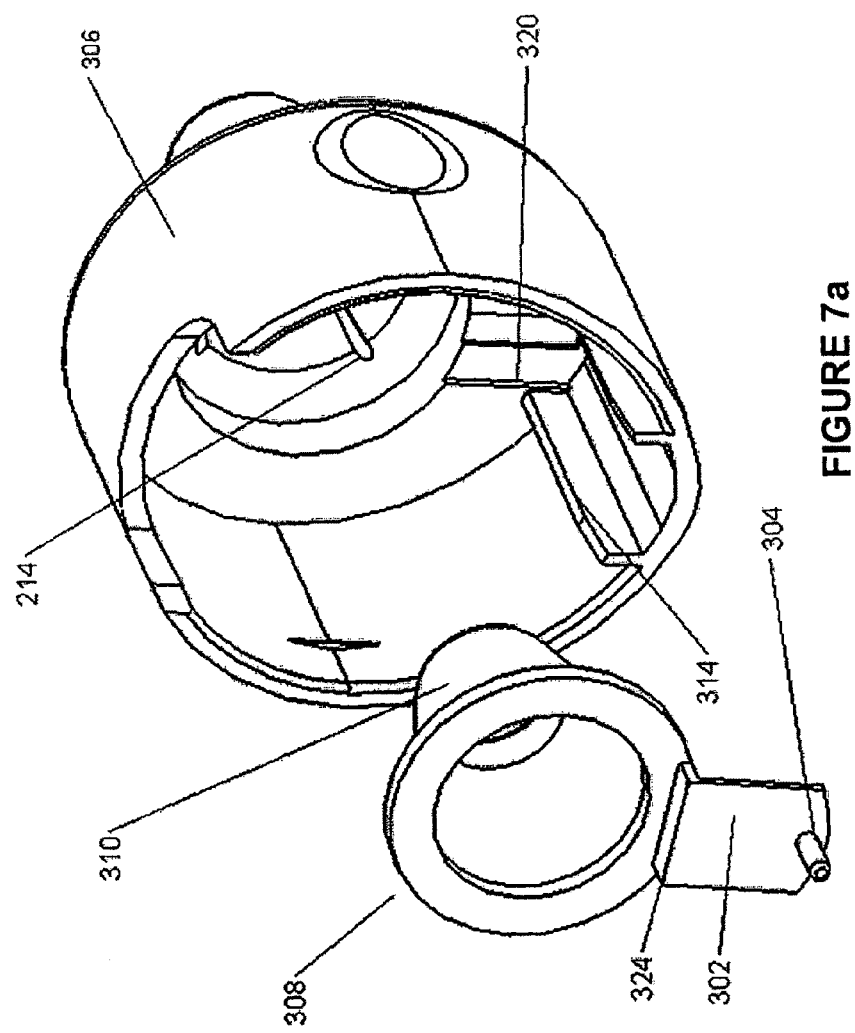
FIGS. 7a-b present alternative embodiments of a removable multi-channel applicator nozzle.

FIG. 7A shows alternative embodiments of the nozzle liner 308 and the nozzle body 306. The nozzle liner 308 includes, among other things, a tubing connection port 304, a cover 302, an outer surface 310. The tubing connection port 304 is another variation of a connector 210 and provides another means (opening) by which fluid may flow from the exterior of the applicator to the plurality of channels. In certain embodiments, the opening that is in fluid communication with the plurality of channels comprises a connector or a connection port. When present, the connector or connection port may be located in any place and at any angle relative to the nozzle body. In certain embodiments, the connector or connection port are rigid and are made of the same material as the nozzle body and/or nozzle liner. In other embodiments, the connector or connection port are flexible. Further, the opening by which fluid may flow from the exterior of the applicator to the plurality of channels may be an opening in the nozzle body or an opening in the nozzle liner.

Figure 7B:
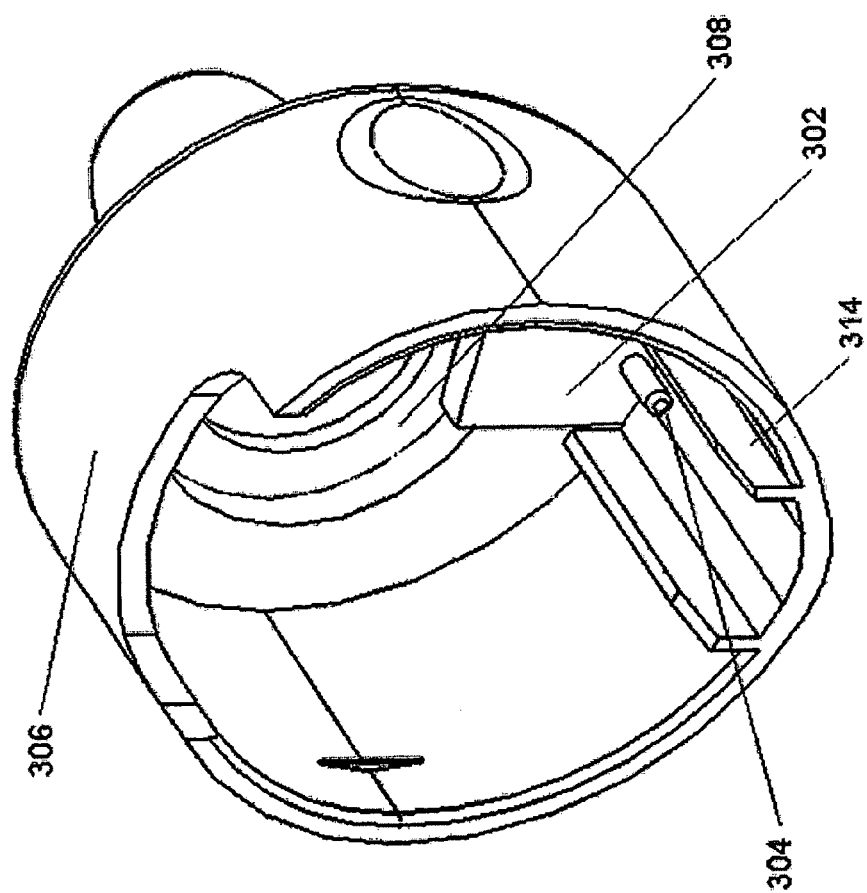
Figure 7C:
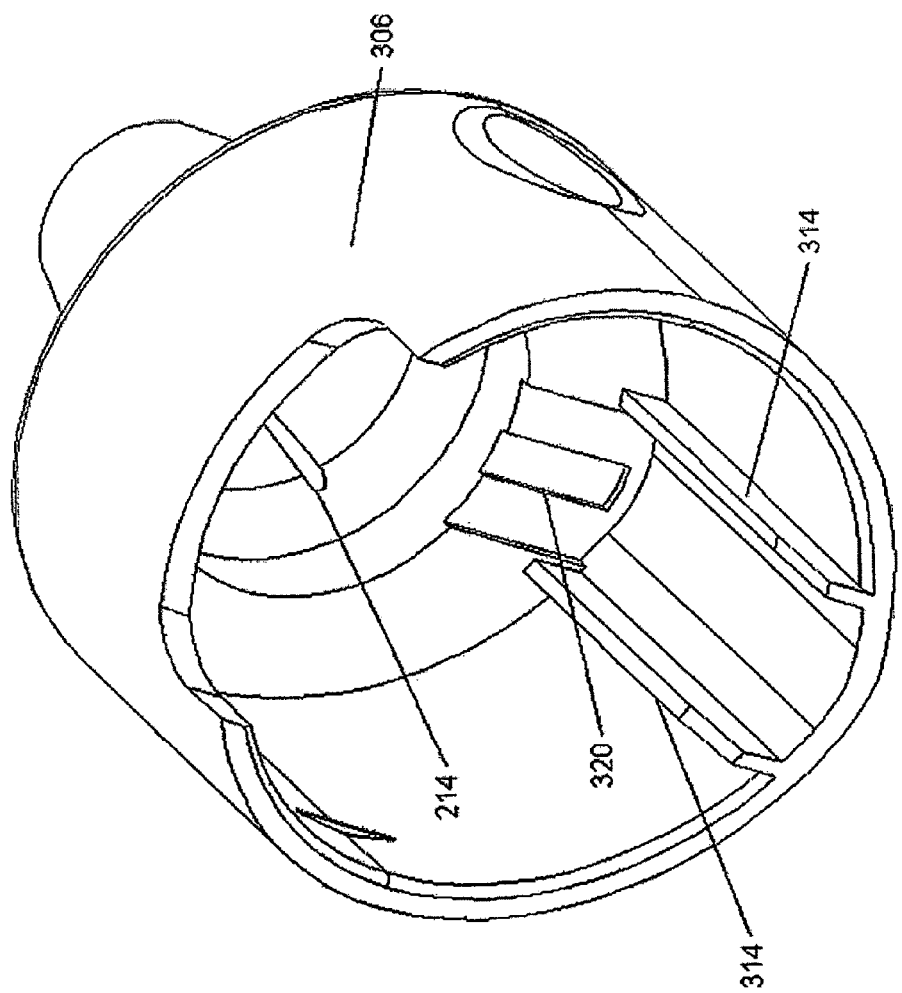

The nozzle liner 308, in some embodiments, includes a snap-fit locking feature (not shown) to create a snap-fit between the nozzle liner 308 and the nozzle body 306. In certain embodiments, the nozzle body 306 includes horizontal walls 314 for receiving the nozzle liner 308 as shown in FIG. 7B. The nozzle body 306 also includes a fluid path groove 320 for receiving the fluid. The fluid from the tubing 116 flows into the tubing connection port 304 and travels vertically in the fluid path groove 320. The fluid then flows into the space 326 (FIG. 7D) defined by the cover 302 and an inner rim 322 of the nozzle body 306. The space 326 results when the horizontal portion 324 of the cover 302 is positioned against the inner rim 322 having a radius. The fluid, then flows from the space 326 to the passageway (not shown) created between the nozzle liner 308 and the nozzle body 306. From the passageway, the fluid enters the inlets 226 of the channels 214 as, for example, described above with regard to FIG. 2. In other words, an opening, for example an opening in the connection port 304, is in communication with the plurality of channels so that fluid may flow via the opening to the plurality of channels.

In some embodiments, the inlets 226 may be aligned away from the space 326 (FIG. 7D). If a single inlet of the channel is in direct communication with the space 326, the fluid may be unevenly distributed amongst the plurality of the inlets. Therefore, in some embodiments, the inlets 226 of the channels are positioned away from the space 326. In certain embodiments, the passageway may have a similar cross-sectional shape as shown in FIG. 2c. The fluid exits the channels 214 and coats the tip portion 706 of the transducer assembly 108. As described above, embodiments of nozzle bodies comprising a plurality of channels having any of a number of sizes, shapes, and positions relative to each other are contemplated. In certain embodiments, the nozzle body comprises 2, 3, 4, 5, or 6 channels. In certain embodiments, the plurality of channels is etched, embedded, or otherwise disposed on the interior surface of the nozzle body. In other embodiments, all or a portion of the plurality of channels extends to the exterior surface of the nozzle body.

In this embodiment, the nozzle body 306 additionally includes a snap-fit indent (not shown) for locking the nozzle liner 308 in place. However, in other embodiments, the nozzle liner 308 may be welded to the nozzle body 306 to create a tight seal between the nozzle liner 308 and the nozzle body 306.

Figure 8A:
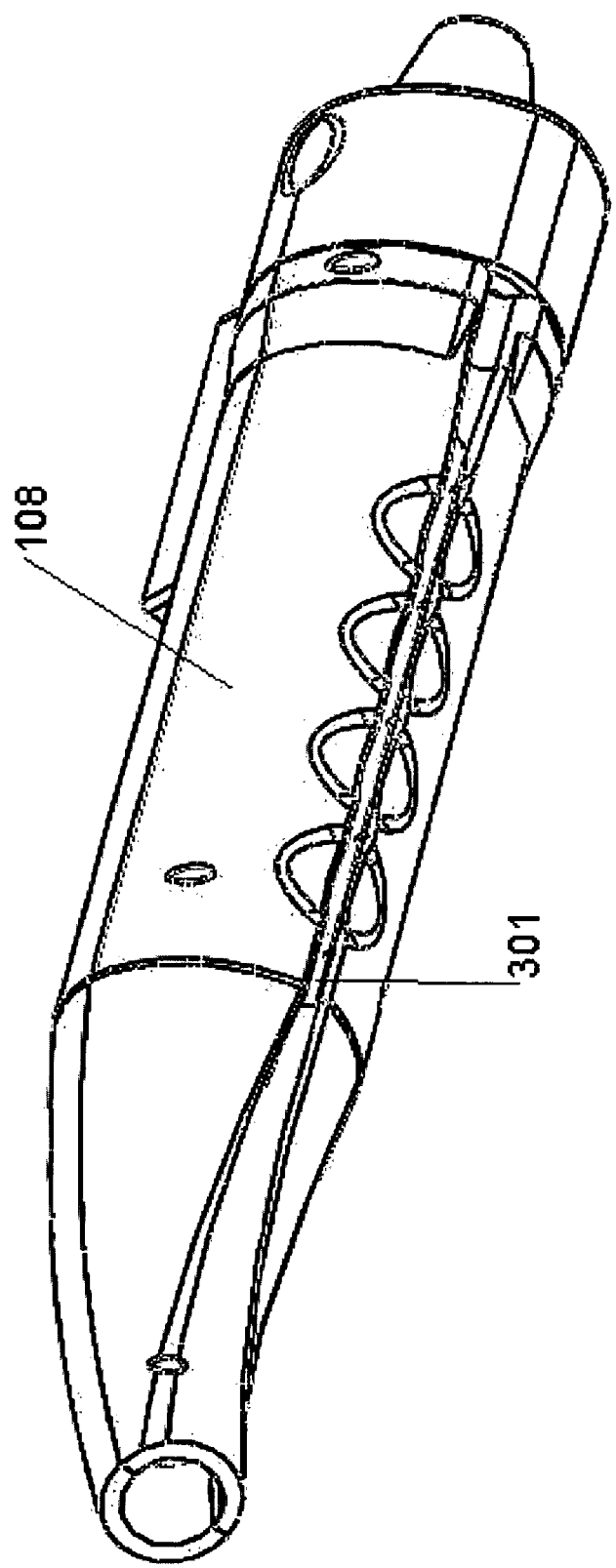
FIG. 8a presents a perspective view of a transducer assembly showing a groove for receiving a tubing.
Figure 8B:
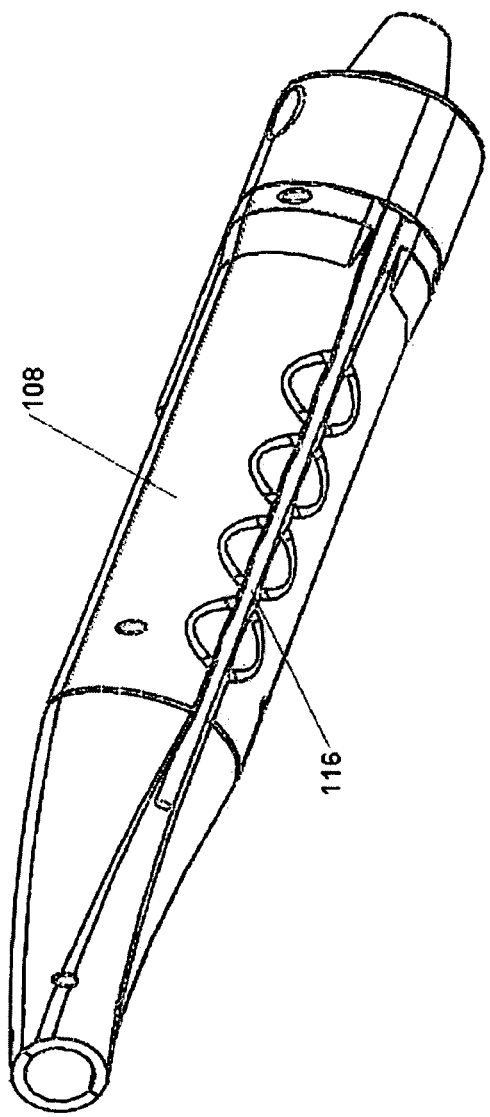
FIG. 8b presents a perspective view of the transducer assembly shown in FIG. 8A with the tubing in place.

FIGS. 8A and 8B show the transducer assembly 108 having a groove 301 for placing the tubing 116. In some embodiments, the tubing 116 is about 10 feet in length. In this embodiments, the tubing 116 is placed in the groove 301 along the transducer assembly 108. The free portion of the tubing 116 may be wrapped around the end of the transducer assembly 108. The transducer assembly 108 may also include a clip (not shown) or other equivalent device for holding the wrapped tubing 116 in place. Where the fluid container is not directly affixed to or housed within the transducer assembly, having the tubing fitted to the transducer assembly facilitates the placement of the fluid container in any convenient location without being bound by the transducer assembly location. Having the tubing out of reach from a user may also minimize inadvertent damage to the tubing. In addition, the user may move and/or hold the transducer assembly with more freedom.

FIG. 9a illustrates an exemplary ultrasound wound therapy device having an applicator 100 connected to a transducer assembly 108. FIG. 9b shows a cross-sectional view of a portion of an applicator 100 being connected to a transducer assembly 108. In addition, FIG. 9 shows a fluid container 114 coupled to the connector 210 of the nozzle 102 through the flexible tubing 116. The transducer assembly 108 is aligned and coupled to the nozzle 102, for example, by aligning slots and pins or by a snap-fit. The distal end 704 (FIG. 9b) of the transducer assembly 108 is then inserted through the proximal portion 202 of the nozzle 102, continues through the distal portion 204 of the nozzle 102, and out through the distal opening 232 (FIG. 9b) of the liner of the nozzle 102.

FIG. 9b also shows a distal end 704 of the transducer tip portion 706 of the transducer assembly 108 extending longitudinally past the distal opening 232 of the nozzle liner 208, but not to a location that is distal to the distal opening 212 of the nozzle 102. That is, when the applicator 100 is engaged to the transducer assembly 108, the distal end 704 of the transducer assembly 108 extends between the distal opening 232 of the nozzle liner 208 and the distal opening 212 of the nozzle 102. In other words, the distal end 704 of the transducer assembly 108 does not protrude out of the nozzle 102 (the distal end 704 of the transducer assembly 108 is proximal to the distal most portion of the applicator). In such embodiments, an operator or patient cannot inadvertently contact the transducer tip portion 706. Given that the transducer tip portion 706 (including the distal end 704) vibrates during use, inadvertent contact with the vibrating transducer tip portion 706 may cause injury to a user or damage the device.

In certain embodiments, a longitudinal separation distance 708, shown in FIG. 9b, between the distal end 704 of the transducer tip portion 706 of the transducer assembly 108 and the distal opening 212 of the nozzle 102 is specified to optimize fluid atomization. This longitudinal distance 708 is hereinafter referred to as a "recess distance." As the recess distance 708 between the distal end 704 of the transducer assembly 108 and the distal opening 212 of the nozzle 102 decreases, the spray pattern may cover a larger wound site area. In addition, with the decreased recess distance, for example less than 0.150 inches, the fluid is less likely to collide at the interior surface 208 of the nozzle 102 before exiting the nozzle 102. This collision may lead to a possible build up of cavitation, or bubbling that may not be atomized, thus causing the fluid to drip from the nozzle 102. Therefore, with the decreased recess distance, the fluid may be less likely to drip from the applicator 100. In some embodiments, if the recess distance is greater than 0.150 inches, the fluid may be more likely to collide with the interior surface 222 of the nozzle body 206 as it exits from the distal end 704 of the transducer assembly 108. In certain embodiments of a three-channel nozzle design, as shown in FIG. 4a, the recess distance 708 may be about 0.06 inches or less. In certain embodiments of a four-channel nozzle design, as shown in FIG. 2, the recess distance 708 may be about 0.05 inches or less. However, other recess distances are possible and are within the scope of the present disclosure.

Referring to FIG. 9b, in certain embodiments, a longitudinal separation distance 710 between the distal opening 232 of the nozzle liner 208 and the distal end 704 of the transducer assembly 108 is also specified, hereinafter referred to as an "extension distance." This extension distance 710 specifies the location on the tip portion 706 of the transducer assembly 108 to which the fluid contacts after the fluid exits from the outlets 230 of the channels 214 (FIG. 2). An optimized extension distance 710 may maximize the range of motion for using the wound therapy device without compromising the quality of fluid atomization. For example, for a three-channel nozzle 102, an extension distance 710 between about 0.03 inches and about 0.09 inches may allow the wound therapy device to be used in any orientation with respect to the wound site while still achieving an optimal spray pattern having minimal fluid dripping from the applicator 100. For a four-channel nozzle 102, a preferred extension distance 710 may be between about −0.065 inches and about 0.09 inches. It should be noted that a negative extension distance 710 implies that the distal end 704 of the transducer assembly 108 is proximal to the distal opening 232 of the nozzle liner 206.

In certain embodiments, a longitudinal separation distance between the distal end 704 of the tip portion 706 of the transducer assembly 108 and the surface or object to be sprayed is a non-contact distance of at least 0.1 inches (2.5 mm). Preferably, the separation distance is from about 2.5 mm to about 51 cm, more preferably, from about 15 mm to about 25 mm. In certain embodiments, as shown in FIG. 2, the non-contact distance can be similarly described as the distance between a distal-most edge 106 of the applicator 100, and the surface or object to be sprayed. In certain embodiments, the non-contact distance from the distal-most edge 106 of the applicator 100 to the surface to be sprayed is at least about 2.5 mm or at least about 5 mm. In other embodiments, the non-contact distance from the distal-most edge 106 of the applicator 100 to the surface to be sprayed is from about 5 mm to about 15 mm.

In certain implementations, a nozzle face 104 is further coupled to the wound therapy device. A nozzle face 104 of the applicator 100, such as an energy reflector depicted in FIGS. 2b-c, may be coupled to the distal nozzle opening 212 or distal end or distal portion of the nozzle 102. The nozzle face 104 is optional and is not required for use of the nozzle. In certain embodiments, the nozzle face is detachable such that the applicator can be used with or without the nozzle face or can be used with a different nozzle face. In other embodiments, the nozzle face is permanently coupled to the nozzle. For example, the nozzle and the nozzle face may be cemented or otherwise affixed, or the nozzle and nozzle face may be molded or machined as a single unit.

As depicted in FIG. 2C, the nozzle face 104 has a proximal region 216, a distal region 240, and a distal nozzle face opening 220, where a diameter of the proximal region 216 of the nozzle face 104 is adapted to be smaller than a diameter of the distal region 240. In this configuration, the nozzle face 104 may serve as an energy reflector. Without being bound by theory, the parabolic shape of the energy reflector nozzle face 104 may help to create and/or maintain a standing wave pattern in a medium between the wound therapy device and a wound site. Specifically, this standing wave pattern may be created based on the interference of the incident ultrasound waves delivered from the applicator 100 to the wound site and the waves reflected from the wound site. The creation and/or maintenance of a standing wave pattern may help prevent interference between the incident and reflected ultrasound waves. As a result, use of an energy reflector may facilitate efficient delivery of more uniform ultrasonic energy. In certain embodiments, the parabolic energy reflector nozzle face 104 may be interchanged with a different nozzle faces 104 for treating different types of wounds, which may require different patterns and/or coverage area of ultrasound energy contact.

In some embodiments, the proximal portion 216 of the nozzle face 104 slides over a distal portion 204 of the nozzle 102 and is secured into place via, for example, aligning slots (not shown) and aligning pins (not shown) disposed over surfaces of the energy reflector 104 and the nozzle 106, respectively. By way of further example, the nozzle face 104 and the nozzle 102 may be coupled by a snap fit or a half-turn closure.

Figure 10B:
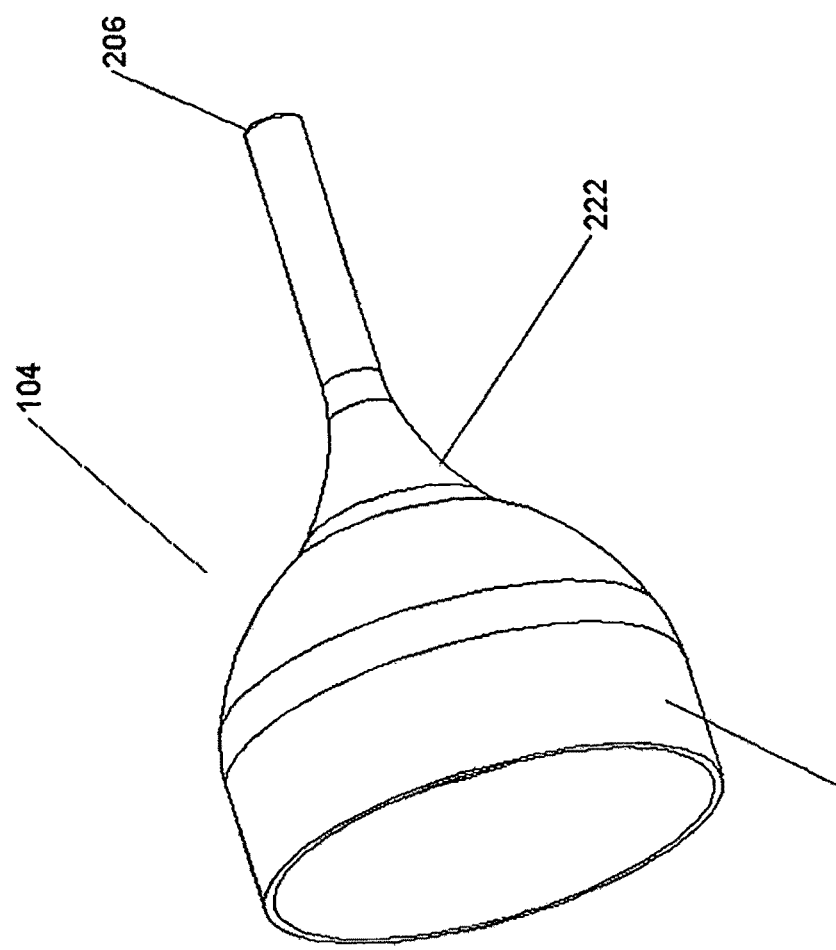
FIG. 10a-b present perspective views of a plurality of applicator nozzle faces of alternative embodiments.
Figure 10A:
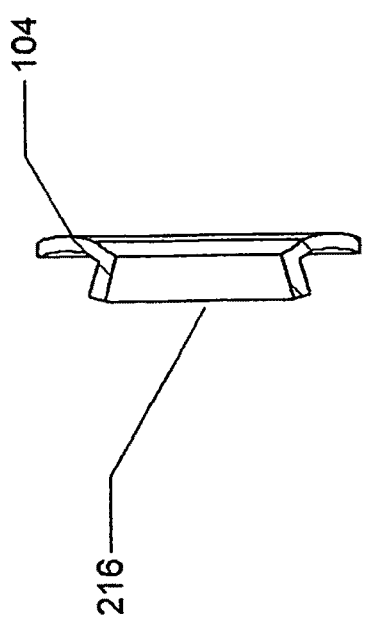

Nozzle faces 104 of different shapes and sizes may be used to provide different treatment conditions or to treat different types of wounds. A nozzle face 104 may also further decrease the likelihood of inadvertent contact between the tip portion 706 of the transducer assembly 108 and a patient or an operator of the transducer assembly 108. In one example, a nozzle face 104 having a parabolic shape, such as the parabolic nozzle face 104 of FIG. 2, is used to create a standing wave pattern in the medium between the transducer assembly 108 and the wound site, which focuses the delivery of high-density ultrasound energy to a specific treatment area. In contrast, the nozzle face 104 depicted in FIG. 10*a* is relatively flat and has a relatively small longitudinal extent. This nozzle face 104 operates by dispersing low-density ultrasound energy over a treatment area that may be wider than the intended treatment area of the parabolic-shaped nozzle face 104 of FIG. 2. In yet another example depicted in FIG. 10*b*, a removable nozzle face 104 may be attached to the distal nozzle opening 212 or distal end or distal portion of the nozzle 102 to focus the delivery of ultrasonic energy to a treatment area smaller than that of the parabolic-shaped nozzle face of FIG. 2. In particular, the diameter of the proximal region 216 of the nozzle face 104 is substantially larger than the diameter of the distal region of the nozzle face 104. This nozzle face 104 may be used to treat wounds in areas of the body that are difficult to reach, such as in a patient's ear, nose, mouth, or throat.

The foregoing examples are merely illustrative of the range of nozzle faces that can be used in combination with the nozzle provided herein. Any of the foregoing nozzle faces can be readily used to optimize treatment of a particular patient or a particular type of wound. In certain embodiments, the applicator comprises a nozzle interconnected to a nozzle face. For example, the nozzle face may be interconnected to the nozzle body via the distal opening, distal portion, or distal end of the nozzle body.

Although not depicted, the fluid container may also be directly affixed to or housed within the transducer assembly. For example, a disposable or re-fillable fluid cartridge may be directly affixed to or housed within the transducer assembly. Regardless of whether the fluid container is a bag (such as a standard IV bag), a cartridge, or a bottle, fluid flow to the applicator can be modulated with, for example, a clamp, a valve, a peristaltic pump, or the like. In certain embodiments, fluid flow is regulated by an on/off switch located on the transducer assembly or the generator. In certain embodiments, a single on/off switch controls fluid flow and the ultrasound transducer. In other embodiments, separate switches or mechanisms control fluid flow and the ultrasound transducer.

The fluid provided to and sprayed from the transducer assembly may be of any appropriate carrier, such as saline, water (regular or distilled), or oil (such as a vegetable, peanut, or canola oil), optionally with a soluble pharmaceutical (e.g., an antibiotic), antiseptic, conditioner, surfactant, emollient, or other active ingredient. The fluid can also be a combination of two or more fluids and/or substances having microscopic particles, such as powder and the like. Exemplary fluids include, but are not limited to, sterile water, saline solution, oil, oxygenated water, hypochlorous acid, or other isotonic or hypertonic solutions. Exemplary fluids may, in certain embodiments, further include drugs (e.g., therapeutic agents) such as antibiotics, anti-fungals, anti-virals, growth factors, analgesics, angiogenesis promoting agents, anti-inflammatory agents, narcotics, and the like, formulated in any of the foregoing fluids or in other pharmaceutically acceptable fluids appropriate for the formulation of the particular drug. However, in certain embodiments, the fluid does not include a therapeutic drug. The fluid may be sterilized so that, in use, a spray of a sterile solution can be administered to patients. In certain embodiments, the fluid further includes one or more preservatives appropriate for extending the shelf-life of the fluid.

In certain other embodiments, the applicator can be used "dry" to deliver ultrasound energy is the absence of fluid or other coupling medium. Regardless of whether the applicator is used to deliver ultrasound energy "wet" or "dry", the applicator can be used to provide ultrasound therapy as part of a therapeutic regimen where one or more additional treatment modalities are also administered.

As can be appreciated, the apparatus, as described, is compatible for use with a pressurized system for delivering pressurized fluid to the transducer assembly 108. An exemplary pressurized system is depicted in FIG. 3. In contrast to a gravity-feed system which requires the source of the fluid to be above the transducer assembly 108, the pressurized fluid delivery system of the present disclosure permits the fluid to be supplied to the transducer assembly 108 from any location or orientation with respect to the body of the transducer assembly 108.

A gravity feed system may also be utilized with the devices of the present disclosure. For example, the applicator 100 may additionally include a cup that is designed to hold a fluid bottle in a relative upright position above the nozzle 102. This cup may be coupled to the nozzle 102 via the connector 210 which may include a valve structure for controllably supplying the fluid from the bottle to the nozzle 102. Alternatively, a fluid bottle or other fluid source may be directly interconnected to the connector or other opening in the absence of a cup, but optionally including a valve. An exemplary gravity-feed system is described in detail in U.S. patent application Ser. No. 11/473,934, the entire contents of which is incorporated by reference herein.

However, using a fluid container 114 and a pressurized fluid delivery system (e.g., pump 404 shown in FIG. 3) may be advantageous for treating wounds for which having a bottle affixed to the applicator may interfere with accessing the particular wound site. It may also be useful to use the fluid container 114 and a pressurized fluid delivery system in situations where greater range of motion of the transducer assembly 108 is desired and/or where treatment requires the use of a larger quantity of fluid (i.e., the fluid container 114 may hold more fluid than the bottle). The term 'greater range of motion' is meant to indicate that the operator has increased flexibility to effectively deliver treatment while holding the applicator and/or transducer assembly at any of a number of possible angles relative to the treatment surface.

In certain other embodiments, a fluid container of virtually any size or shape is contemplated. However, given that larger containers are relatively heavy when filled with fluid, the fluid container may be placed on a counter-top, cart, or hung from a pole. In one implementation, the fluid container rests or is affixed to the same cart upon which the ultrasound wound therapy device sits. In another embodiment, the fluid container is affixed to or housed within the generator.

Additionally, in certain embodiments, the applicators 100 are disposable, and can be readily removed from the transducer assembly 108 and changed between patients or changed between each use even for the same patient. In certain embodiments, an applicator 100 is changed between each patient. Changing the applicator 100 between uses, such that each wound is treated with a fresh applicator 100, prevents contamination between patients or between wound sites on the same patient.

In certain embodiments, the applicator 100 and/or ultrasound wound therapy device contain means for encouraging or requiring that the applicator 100 be replaced following a single use. In other words, the applicator 100 and/or the ultrasound wound therapy device comprises means such that, once an applicator is engaged to a transducer assembly and then removed, the operator is prevented or discouraged from subsequently re-engaging the same applicator to a transducer assembly. Single use of the applicator 100 is recommended by the manufacturer to prevent non-sterile use and/or cross-contamination between patients. For example, a message can be displayed by an LCD or other display located on the ultrasound wound therapy device to remind and encourage user compliance with the recommended use of the applicator 100. Alternatively or additionally, the applicator 100 or ultrasound wound therapy device may include means for preventing nozzle re-use. In other words, the applicator 100 or ultrasound wound therapy device may include a mechanism that inhibits or prevents an operator from using a single applicator 100 to treat multiple patients and/or multiple wounds. Exemplary mechanisms for providing such preventive measures, including for example, an IC chip, a timer, an expanding foam, and/or a radio frequency tag 720 and corresponding radio frequency tag reader 722 (FIG. 3), are described in detail in the U.S. patent application Ser. No. 11/473,934, the entire contents of which are incorporated herein by reference.

In certain embodiments, the nozzle 102 may include a locking device 730 (FIGS. 2c and 2e) to prevent re-coupling of the transducer assembly 108 to the applicator 100. The locking device 730 may be pre-assembled to the nozzle 102 and remain in a ready-to-be used position prior to use. In some embodiments, as the transducer assembly 108 couples to the applicator 100, the locking device 730 shifts to an open position and remains in this position during the operation. Following the de-coupling of the transducer assembly 108 from the applicator 100, the locking device 730 shifts to a closed position. In the closed position, an arm 732 (FIG. 2e) from the locking device 730 may protrude through an aperture (not shown) located on the nozzle 102 to prevent the transducer assembly 108 from coupling to the applicator 100 again. U.S. patent application Ser. No. 12/004,636, the disclosure of which is incorporated by reference in its entirety, provides an exemplary locking device 730.

In certain embodiments, the liquid spray from the ultrasound wound therapy device provides significant improvements for wound care and patient comfort during treatment. Specifically, the fluid spray produced from the applicator 100 has a uniform particle size, thus enhancing the efficiency with which the ultrasound energy is carried to the wound site. In addition, the non-contact distance from which the ultrasound energy and the fluid spray is delivered to the wound site results in beneficial effects including, but not limited to, decreased healing time, improved healing (e.g., more complete wound closure), and decreased incidence of infection. Without being bound by theory, this may be due to the ability of the emitted ultrasound energy and/or the fluid spray to penetrate the wound tissue to a beneficial depth. Additionally, action of the ultrasonic energy and/or the fluid spray at the wound surface may contribute to the therapeutic effect. Furthermore, the liquid spray may be delivered at a temperature that does not result in substantial heating of the wound tissue, which minimizes aggravation of the wound. Given that the ultrasound energy and/or fluid spray is delivered without direct contact with the treated patient tissue and without significantly increasing the temperature of the treated tissue, patient tissue can be treated with little or no pain relative to any treatment modality that involves contact with the subject tissue.

The applicator 100 or ultrasound wound therapy device may optionally be provided with a laser or ultrasonic transducer for measuring the non-contact distance or stand-off distance from a wound surface. A feedback control mechanism can also be provided for indicating whether the measured non-contact distance is suitable for effecting optimum beneficial bactericidal, therapeutic and/or other effects. The feedback assembly is integrated with the transducer assembly 108 and corresponding electronics housed within an ultrasonic generator 110 for obtaining the measured non-contact distance data and processing the data to determine whether the measured non-contact distance is optimum for treatment purposes. If the non-contact distance is determined not to be the optimum non-contact distance, the feedback control mechanism can sound an audible alarm or display a message on a display, such as an LCD display. The alarm or message can indicate if the non-contact distance should be decreased or increased. If the nozzle 102/ultrasound wound therapy device is mounted to a robotic arm, the feedback control mechanism can in turn control the robotic arm for increasing or decreasing the non-contact distance.

Regardless of the particular mechanism of action, the delivery of ultrasonic energy and a fluid spray at a non-contact distance improves wound healing and decreases infection. Briefly, emitted energy and the fluid spray are applied to the wound. In certain embodiments, the energy and fluid spray are applied for a treatment time proportional to the size of the wound. For example, the approximate size of the wound can be inputted into the ultrasound wound therapy device and the device sets a treatment time based on the size of the wound. The ultrasound wound therapy device may also be able to recommend an appropriate applicator nozzle face for providing the suitable ultrasonic energy pattern and/or intensity to treat such wound. Generally, treatment times vary from approximately 5 minutes to approximately 30 minutes. However, shorter and longer treatment times are contemplated. For example, in certain embodiments, the treatment time is approximately 2 minutes or approximately 3 minutes. As described above, nozzle faces 104 of different sizes and shapes may also be used to treat different types of wounds. For example, a small wound situated in an area of the body that is difficult to reach may be treated with a nozzle face 104, as depicted in FIG. 10b whereas a large surface wound may be treated with a nozzle face 104, as depicted in FIG. 2c.

According to one illustrative treatment regimen, once emitted energy and fluid spray are emerging from the applicator 100, the operator can direct the energy and spray to the wound. In one recommended embodiment, the wound is treated by slowly moving the applicator 100 head back and forth and/or up and down (at a non-contact distance) across the wound. The spray pattern may be, for example, serpentine or substantially checkerboard in pattern. This delivery method has two advantages. First, this method helps insure that ultrasonic energy and liquid spray are delivered to the entire wound. Second, this method may help prevent operator fatigue that would likely result if the device was held in substantially the same place throughout the treatment. In one embodiment, the applicator 100 is held such that the ultrasonic energy and liquid spray are delivered substantially normal to the surface of the wound. In an alternative embodiment, the applicator 100 can be held at any position or angle in relation to the surface of the wound. Additionally, the spray pattern may include moving the applicator 100 in-and-out relative to the wound surface (e.g., varying the distance from the wound while maintaining a non-contact distance). Such a spray pattern helps ensure that a wound, which varies in depth across its surface area, is treated at an effective distance. The spray pattern may also be varied by using an appropriate nozzle face 104 designed to facilitate the production of certain spray pattern.

In certain embodiments, the ultrasound energy is delivered in the absence of a liquid spray or coupling agent. Delivery of ultrasonic energy in the absence of a liquid spray or coupling agent is sometimes referred to herein as "dry" delivery.

Regardless of whether the ultrasound energy is delivered "wet" or "dry", in certain embodiments, the treatment with ultrasound energy is part of a therapeutic regimen combining one or more additional treatment modalities. Exemplary additional modalities include, but are not limited to, negative pressure therapy, topical anti-bacterial ointments, systemic antibiotics, silver-based creams, and dressings. Furthermore, the methods of the present invention may be used in combination with physical therapy, occupational therapy, psychological therapy, diet, and exercise. When used in combination with any topical medicaments, the topical medicament may be applied prior to and/or following treatment with ultrasound energy.

In one embodiment, the need for a human operator is eliminated. The transducer assembly 108 is affixed to a robotic arm programmed to direct the emitted energy and liquid spray to the wound.

As outlined above, in certain embodiments the emitted ultrasonic energy and fluid spray are applied to the wound for a treatment time proportional to the size of the wound. In one embodiment, the invention provides a treatment algorithm for selecting treatment time based on the size of the wound. The time for each treatment is selected based on the area of the wound. For example, the area of the wound is calculated by measuring the length of the wound (at its greatest point) and the width of the wound (at its greatest point and perpendicular to the length). The length and width of the wound can be measured, for example, in centimeters. The area of the wound (in square centimeters) is calculated by multiplying the length times the width of the wound. The treatment time is proportional to the area of the wound. Similarly, treatment time may be calculated based on a treatment area when, for example, the area to be treated is not a wound or when treatment of an area that is larger or smaller than the actual wound is indicated.

Based on the algorithm, the following approximate treatment times may be selected based on wound size: 3 minutes for wounds with an area of less that 10 cm$^2$; 4 minutes for wounds with an area of 10-20 cm$^2$; 5 minutes for wounds with an area of 20-30 cm$^2$; 6 minutes for wounds with an area of 30-40 cm$^2$; 7 minutes for wounds with an area of 40-50 cm$^2$; 8 minutes for wounds with an area of 50-60 cm$^2$; 9 minutes for wounds with an area of 60-70 cm$^2$; 10 minutes for wounds with an area of 70-80 cm$^2$; 11 minutes for wounds with an area of 80-90 cm$^2$; 12 minutes wounds with an area of 90-100 cm.

In certain embodiments, the ultrasonic wound therapy device is programmed with the algorithm. The operator enters the wound size into the device using a keypad. A treatment time is selected based on the wound size. In certain embodiments, the ultrasound wound therapy device includes a timer that counts down from the treatment time. When the treatment time has elapsed (e.g., the timer has ticked down to zero), the ultrasound wound therapy device may automatically shut off. In other words, after the treatment time has elapsed, the power shuts off and the transducer stops vibrating. It is appreciated that a timer and automatic shut off mechanism have utilities apart from their use in conjunction with treatment times proportional to wound size. Such timers may be used even in the absence of a treatment time algorithm (e.g., a timer can be used when the total treatment time is selected by the individual operator). Additionally or alternatively, an alarm may sound to alert the operator when the treatment time has elapsed.

The above algorithm does not direct the frequency (total number or number/week) of treatments. Furthermore, as the wound heals, the treatment time may be reassessed and recalculated in accordance with the decreasing size of the wound. Additionally, the above treatment algorithm is only one way to select an appropriate treatment time. Wounds may be treated for a longer or shorter period of time than that recommended based on the treatment algorithm. Similarly, the generator can be modified to incorporate additional or alternative treatment algorithms.

Further, the above algorithm is merely exemplary. Other treatment algorithms can be used based on, for example, the severity of the wound, the cause of the injury, the area of the body effected, and the health of the patient. Moreover, other treatment algorithms may be appropriate when the applicator is used with an ultrasound therapy device, but for non-wound indications.

The foregoing describes methods for using an applicator 100 with an ultrasound wound therapy device to deliver ultrasound energy and a liquid spray. However, as detailed throughout, an applicator 100 can also be used in methods for treating tissue in which ultrasound energy is delivered in the absence of a liquid spray or coupling agent. The foregoing exemplary features, including the use of a treatment algorithm, various means for preventing re-use of the applicator, and components for determining and maintaining the appropriate non-contact distance from the patient tissue, are equally applicable when the applicator is used in the absence of a liquid spray or coupling medium.

The present invention contemplates a variety of kits. In one embodiment, a kit includes one or more of an applicator 100 (e.g., a nozzle 102, and optionally one or more nozzle faces 104), a fluid bag 114, and flexible or non-flexible tubing 116 sized and shaped to interconnect the fluid bag 114 to the connector 210 of the nozzle 102. The kit may optionally include directions for use and/or one or more sterile swabs. The sterile swabs can be used to wipe, prior to or after use, one or more of: the fluid bag 114, all or a portion of the applicator 100, all or a portion of the tubing 116, all or a portion of the transducer assembly 108, and all or a portion of the ultrasound wound therapy device. In certain examples, the fluid bag 114 includes a sterile fluid suitable for use in the treatment of a wound. Any of the foregoing kits may be sterilized prior to packaging such that the contents of the kit are sterile. The kits can be marked to indicate that they are intended for use with a single patient.

In another embodiment, the kit does not include the fluid bag 114. In certain embodiments, the kit includes the applicator nozzle and tubing, and the operator may use any appropriate fluid bag. In certain other embodiments, the applicator 100 includes a nozzle, a valve and a cup. This kit may be specifically intended for use in conjunction with a bottle. Optionally, this applicator 100 may be packaged with a bottle including a fluid, where the bottle is sized and shaped to fit onto the cup of the applicator 100. This kit may optionally include directions for use and/or one or more sterile swabs.

Kits containing an applicator and any one or more of the foregoing kit components are contemplated. Additionally, kits can be packaged and/or sold alone or with an ultrasound therapy device.

It is to be understood that the foregoing description is merely a disclosure of particular embodiments and is in no way intended to limit the scope of the disclosure. All operative combinations of any of the foregoing aspects and embodiments are contemplated and are within the scope of the invention. Other possible modifications will be apparent to those skilled in the art.

We claim:

1. An applicator for use with an ultrasound transducer assembly, comprising:
   a nozzle body having an interior and an exterior surface;
   a nozzle liner having an interior and an exterior surface and being engageable with the nozzle body such that a plurality of channels are defined at least in part by opposing portions of the exterior surface of the nozzle liner and the interior surface of the nozzle body, each of the plurality of channels having an inlet and an outlet; wherein the nozzle body and the nozzle liner are sized and shaped to releasably interconnect with the ultrasound transducer assembly;
   a passageway defined by a space between the nozzle body and the nozzle liner, in fluid communication with the inlets of each of the plurality of channels; and
   an opening sized and shaped for introducing fluid to the passageway to provide fluid flow from the outlet of each of the plurality of channels to an ultrasound transducer of the ultrasound transducer assembly essentially simultaneously such that the ultrasound transducer atomizes the fluid.

2. The applicator of claim 1, wherein the opening comprises a connector extending from an exterior surface of the nozzle body to an opening on an interior surface of the nozzle body, whereby the fluid can flow through the connector into the passageway.

3. The applicator of claim 1, wherein the inlet of at least one of the plurality of channels has a diameter that is larger than a diameter of the outlet of said channel.

4. The applicator of claim 1, wherein the inlet of at least one of the plurality of channels has a diameter approximately equal to a diameter of the outlet of said channel.

5. The applicator of claim 1, wherein the opening is sized and shaped for introducing fluid to the inlets of the plurality of channels through the passageway.

6. The applicator of claim 1, wherein at least one of the plurality of channels is arranged in a spiral winding fashion about the center axis of the nozzle body.

7. The applicator of claim 1, wherein the plurality of channels is on the interior surface of the nozzle body.

8. The applicator of claim 1, wherein the plurality of channels is three channels.

9. The applicator of claim 1, wherein the plurality of channels is four channels.

10. The applicator of claim 1, wherein the plurality of channels is five channels.

11. The applicator of claim 1, wherein the applicator is coupled to an ultrasound transducer having a transducer tip portion.

12. The applicator of claim 11, wherein a distal end of the transducer tip portion of the ultrasound transducer is distal to an opening defined by a distal end of the nozzle liner.

13. The applicator of claim 12, wherein the transducer tip portion of the ultrasound transducer extends between the distal opening of the nozzle liner and the distal opening of the nozzle body, and wherein the distal most tip of the transducer tip portion is proximal to the distal end of the applicator.

14. The applicator of claim 11, wherein the fluid contacts a plurality of sections around a circumference of the transducer tip portion of the ultrasound transducer.

15. The applicator of claim 1, further comprising a tubing in communication with the opening.

16. The applicator of claim 15, further comprising a fluid container that is coupled to the tubing.

17. The applicator of claim 1, wherein fluid flow is pressurized.

18. The applicator of claim 17, wherein fluid flow is pressurized by a peristaltic pump.

19. The applicator of claim 1, wherein the applicator further includes a nozzle face, wherein the nozzle face comprises a proximal portion engageable with a distal opening of the nozzle body.

20. The applicator of claim 19, wherein the nozzle face includes a proximal portion and a distal portion, wherein the diameter of the proximal portion is smaller than the diameter of the distal portion.

21. The applicator of claim 19, wherein the nozzle face includes a proximal portion and a distal portion, wherein the diameter of the proximal portion is larger than the diameter of the distal portion.

22. The applicator of claim 1, wherein the plurality of channels are formed on the exterior surface of the nozzle liner.

23. The applicator of claim 1, wherein a first portion of each of the plurality of channels is formed on the interior surface of the nozzle body and a second portion of the each of the plurality of channels is formed on the exterior surface of the nozzle liner.

24. The applicator of claim 1, wherein the outlets of the plurality of channels are equidistantly spaced apart from one another.

25. The applicator of claim 1, further comprising: a locking device having an arm configured to prevent the nozzle body from coupling to the transducer assembly a second time.

26. The applicator of claim 25, wherein the locking device is initially configured in an open position allowing the nozzle body to couple to the ultrasound transducer, and upon separation from the ultrasound transducer the locking device shifts to a closed position to prevent the nozzle body from coupling to the ultrasound transducer a second time.

27. The applicator of claim 25, further comprising: a radio frequency tag reader;

wherein the locking device includes a radio frequency tag that can be read by the radio frequency tag reader such that that the nozzle body can only be mated with the ultrasound transducer for a single treatment.

28. A kit, comprising:
an applicator for an ultrasound device having an ultrasound transducer, the applicator including:
   a sterilized nozzle body having an interior and an exterior,
   a sterilized nozzle liner having an interior and an exterior surface and being engageable with the nozzle body to define a plurality of channels between opposing portions of the interior of the nozzle body and the exterior surface of the nozzle liner, each channel having an inlet and an outlet,
   a passageway in fluid communication with the inlet of each channel defined by a space between the nozzle body and the nozzle liner, and
   an opening sized and shaped to introduce fluid to the passageway to provide fluid flow from the outlet of each of the plurality of channels essentially simultaneously to a tip portion of the ultrasound transducer such that the fluid is atomized; and
a fluid container.

29. The kit of claim 28, further comprising a flexible tubing configured to interconnect the fluid container to the connector of the applicator.

30. The kit of claim 28, wherein said fluid container includes a fluid.

31. The kit of claim 28, wherein said fluid is sterile saline solution.

32. A kit, comprising:
a sterilized applicator for use with an ultrasound transducer assembly, comprising:
   a nozzle body having an interior and an exterior surface,
   a nozzle liner having an interior and an exterior surface and being engageable with the nozzle body such that a plurality of channels are defined at least in part by opposing portions of the exterior surface of the nozzle liner and the interior surface of the nozzle body, each of the plurality of channels having an inlet and an outlet,
   a passageway defined by a space between the nozzle body and the nozzle liner, in fluid communication with the inlets of each of the plurality of channels, and
   an opening sized and shaped for introducing fluid to the passageway to provide fluid flow from the outlet of each of the plurality of channels essentially simultaneously to an ultrasound transducer of the ultrasound transducer assembly such that the fluid is atomized by a surface of the ultrasound transducer; and
tubing.

33. The kit of claim 32, further comprising one or more nozzle face.

34. The kit of claim 32, further comprising a fluid container.

35. The kit of claim 32, wherein the tubing is a flexible tubing.

36. A kit, comprising:
a sterilized applicator for use with an ultrasound transducer assembly, the applicator including:
   a nozzle body sized and shaped to interconnect with the applicator;
   a nozzle liner having an interior and an exterior surface and being engageable with the nozzle body to define at least in part a plurality of channels between opposing portions of the nozzle liner and the nozzle body, each channel having an inlet and an outlet;
   a passageway defined by a space between the nozzle body and the nozzle liner, and in fluid communication with the inlet of each channel;
   an opening sized and shaped to introduce fluid to the passageway to provide fluid flow from the outlet of each of the plurality of channels essentially simultaneously to a tip portion of the ultrasound transducer assembly; and
   at least one nozzle face.

37. A method of delivering ultrasound energy from a non-contact distance, comprising:
providing an applicator including a nozzle body; a nozzle liner having an interior and an exterior surface and being engageable with the nozzle body, such that the nozzle body and the exterior surface of the nozzle liner define at least in part a plurality of channels between opposing portions of the nozzle liner and the nozzle body, each channel having an inlet and an outlet; a passageway defined by a space between the nozzle body and the nozzle liner in fluid communication with the inlet of each channel; and an opening sized and shaped for introducing fluid to the passageway to provide fluid flow from the outlet of each of the plurality of channels to a tip portion of the ultrasound transducer assembly essentially simultaneously such that the tip portion atomizes the fluid; and
delivering ultrasound energy to a tissue from a non-contact distance, wherein the ultrasound energy penetrates the tissue to provide a therapeutic effect.

38. An applicator for a device configured to deliver ultrasound energy via a fluid medium, comprising:
a sterilized nozzle body having an interior and an exterior;
a nozzle liner having an interior and an exterior surface and being engageable with the nozzle body to define at least in part a plurality of channels between opposing portions of the nozzle liner and the nozzle body, each channel having an inlet and an outlet; and
an opening sized and shaped for introducing fluid to a passageway in fluid communication with the inlets of the plurality of channels to provide fluid flow from the outlet of each of the plurality of channels essentially simultaneously to a tip portion of an ultrasound transducer.

39. An applicator for use in treating a wound using ultrasound energy, the applicator comprising:
a nozzle body including a plurality of channels defined between opposing portions of an interior surface of the nozzle body and a nozzle liner removably engaged with the nozzle body, each channel having an inlet and an outlet; and
an opening sized and shaped for introducing fluid to a passageway in fluid communication with the inlets of the plurality of channels to provide fluid flow from the outlet of each of the plurality of channels essentially simultaneously to a tip portion of an ultrasound transducer.

* * * * *

UNITED STATES PATENT AND TRADEMARK OFFICE
CERTIFICATE OF CORRECTION

PATENT NO.         : 8,491,521 B2
APPLICATION NO.    : 12/218760
DATED              : July 23, 2013
INVENTOR(S)        : Peterson Page 1 of 1

It is certified that error appears in the above-identified patent and that said Letters Patent is hereby corrected as shown below:

In the Specification

Column 7, Line 50, place a "." after "FIG. 7b"
Column 8, Line 9, "bums" should be "burns"
Column 19, Line 22, "I 00" should be "100"

Signed and Sealed this
Second Day of June, 2015

Michelle K. Lee
*Director of the United States Patent and Trademark Office*